United States Patent [19]

Hashimoto et al.

[11] Patent Number: 4,906,662

[45] Date of Patent: Mar. 6, 1990

[54] PHENOL DERIVATIVES, THEIR PREPARATION AND THE USE THEREOF

[75] Inventors: Kinji Hashimoto; Kiyoto Goto; Ken-ichi Kanai, all of Naruto; Yoshiaki Tsuda, Anan, all of Japan

[73] Assignee: Otsuka Pharmaceutical Factory, Inc., Naruto, Japan

[21] Appl. No.: 7,044

[22] Filed: Jan. 27, 1987

[30] Foreign Application Priority Data

Sep. 29, 1986 [JP] Japan ................... 61-230484

[51] Int. Cl.⁴ ............... A61K 31/145; C07C 101/34; C07C 101/72; C07C 101/44
[52] U.S. Cl. ................ 514/524; 514/535; 514/539; 514/563; 514/576; 514/603; 514/619; 514/656; 514/657; 514/658; 558/418; 560/16; 560/43; 560/44; 560/45; 560/48; 560/75; 562/454; 562/455; 562/431; 562/433; 562/478; 564/167; 564/171; 564/308; 564/430; 564/433; 564/434
[58] Field of Search ............... 564/308, 430, 433, 434, 564/167, 171; 514/658, 524, 535, 530, 563, 576, 603, 619, 657, 656, 825, 826, 863; 558/418; 562/454, 455, 431, 433, 478; 560/16, 43, 44, 45, 48, 75; 260/513.3

[56]  References Cited

U.S. PATENT DOCUMENTS

| | | | |
|---|---|---|---|
| 4,008,043 | 2/1977 | Kalopissis et al. | 564/434 |
| 4,008,999 | 2/1977 | Kalopissis et al. | 564/167 |
| 4,054,147 | 10/1977 | Kalopissis et al. | 564/433 |
| 4,112,229 | 9/1978 | Kalopissis et al. | 544/105 |
| 4,170,452 | 10/1979 | Grollier et al. | 8/10.2 |
| 4,172,151 | 10/1979 | Moore | 514/658 |
| 4,200,432 | 4/1980 | Kalopissis | 544/105 |
| 4,346,105 | 8/1982 | Sallmann et al. | 514/539 |
| 4,496,590 | 1/1985 | Schlegel et al. | 564/433 |
| 4,510,139 | 4/1985 | Bailey | 564/167 |
| 4,515,980 | 5/1985 | Bailey | 560/45 |
| 4,539,429 | 9/1985 | Bailey | 514/658 |
| 4,568,684 | 2/1986 | Rentzece | 560/44 |
| 4,716,178 | 12/1987 | Scherrer et al. | 562/454 |
| 4,764,619 | 8/1988 | Ganjima et al. | 560/45 |

FOREIGN PATENT DOCUMENTS

| | | |
|---|---|---|
| 211549 | 2/1987 | European Pat. Off. . |
| 212848 | 3/1987 | European Pat. Off. . |
| 1539553 | 9/1968 | France ................... 560/48 |

OTHER PUBLICATIONS

Burmistrov, S. I. et al, *Chemical Abstracts*, vol. 68, No. 86936y (1968).
Chemical Abstracts, vol. 76, No. 15, published Apr. 10, 1972, Abstract No. 85522p, Izard-Verchere et al.

*Primary Examiner*—Richard L. Raymond
*Assistant Examiner*—Raymond Covington
*Attorney, Agent, or Firm*—Armstrong, Nikaido, Marmelstein, Kubovcik & Murray

[57]   ABSTRACT

Disclosed are phenol derivatives of the formula

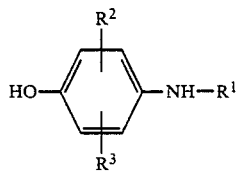

(1)

wherein $R^1$ is a substituted phenyl group, $R^2$ and $R^3$ are $C_1$-$C_6$ alkyl group and of the formula

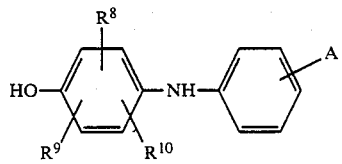

(4)

wherein $R^8$, $R^9$ and $R^{10}$ are $C_1$-$C_6$ alkyl and the like and A is H, $C_1$-$C_6$ alkylsulfonyl and the like substituents. These compounds and some related compounds have anti-inflammatory activity and lipoxygenase inhibitory activity.

11 Claims, No Drawings

PHENOL DERIVATIVES, THEIR PREPARATION AND THE USE THEREOF

This invention relates to phenol derivatives and the salts thereof, processes for preparing the same and the uses thereof, particularly for treating inflammation and for inhibiting lipoxygenase.

The compounds of the invention are selected from the group consisting of:

(1) a phenol derivative of the formula

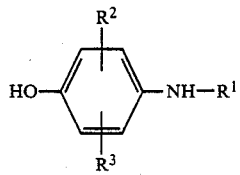
(1)

wherein $R^1$ represents a phenyl group having 1–3 substituents selected from the class consisting of cyano group, carbamoyl group, nitro group, sulfamoyl group, hydroxy-$C_1$-$C_6$ alkyl group, $C_1$-$C_6$ alkoxycarbonyl-$C_1$-$C_6$ alkyl group, carboxy-$C_1$-$C_6$ alkyl group, $C_1$-$C_6$ haloalkyl group, $C_1$-$C_6$ acyl group, $C_1$-$C_6$ alkylthio group, phenylthio group and $C_1$-$C_6$ alkylsulfonyl group, and $R^2$ and $R^3$ each are the same or different and represent $C_1$-$C_6$ alkyl group, and a salt thereof;

(2) a phenol derivative of the formula

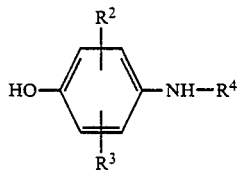
(2)

wherein $R^2$ and $R^3$ are as defined above and $R^4$ represents a tri($C_1$-$C_6$ alkoxy)phenyl group, dihalophenyl group or a group of the formula

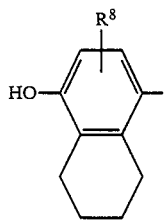

wherein $R^5$ is hydroxy-$C_1$-$C_6$ alkyl or carboxy-$C_1$-$C_6$ alkyl group and $R^6$ is hydroxyl group, halogen atom or $C_1$-$C_6$ alkyl group, and a salt thereof;

(3) a phenol derivative of the formula

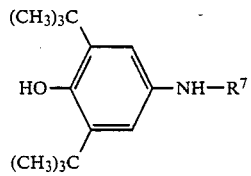
(3)

wherein $R^7$ represents a phenyl group having a substituent selected from the class consisting of fluoro, 2-chloro, $C_1$-$C_6$ alkoxy, carboxyl, n-butyl, amino, hydroxyl and N,N-di($C_1$-$C_6$ alkyl)amino groups, or $R^7$ represents a phenyl group having carboxyl and $C_1$-$C_6$ alkyl groups as the substituent, a phenyl group having carboxyl and hydroxyl groups as the substituents, a phenyl group having carboxyl group and halogen atom as the substituent, a phenyl group having hydroxyl group and halogen atom as the substituent, or a phenyl group having $C_1$-$C_6$ alkoxy and hydroxyl groups as the substituent, and a salt thereof; and (4) a phenol derivative of the formula

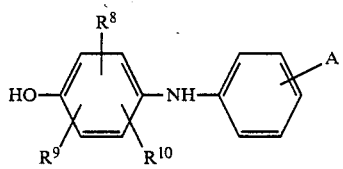
(4)

wherein $R^8$ and $R^9$ are the same or different and each represent $C_1$-$C_6$ alkyl group and $R^{10}$ represents hydrogen atom or $C_1$-$C_6$ alkyl group, or $R^9$ and $R^{10}$, taken together with the phenyl ring to which they are attached, form a fused ring of the formula

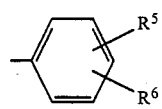

and A represents:
  a hydrogen atom,
  $C_1$-$C_6$ alkylsulfonyl group,
  $C_1$-$C_6$ alkoxycarbonyl group,
  piperidinocarbonyl group,
  phenyl-$C_1$-$C_6$ alkylcarbamoyl group,
  $C_1$-$C_{12}$ alkylcarbamoyl group,
  $C_3$-$C_8$ cycloalkylcarbamoyl group,
  $C_2$-$C_6$ alkenyl group having a substituent selected from the class consisting of $C_1$-$C_6$ alkoxycarbonyl, carboxyl, $C_1$-$C_6$ acyl, $C_1$-$C_6$ alkylcarbamoyl and $C_3$-$C_8$ cycloalkylcarbamoyl groups,
  $C_1$-$C_6$ alkyl group having a substituent selected from the class consisting of $C_3$-$C_8$ cycloalkylcarbamoyl, $C_1$-$C_6$ alkylcarbamoyl, phenyl-$C_1$-$C_6$ alkylcarbamoyl, piperidinocarbonyl, morpholinocarbonyl and hydrazinocarbonyl groups,
  carboxy-$C_1$-$C_6$ alkyl group,
  $C_1$-$C_6$ alkoxycarbonyl-$C_1$-$C_6$ alkyl group,
  $C_1$-$C_6$ alkyl group,
  carboxyl group,
  $C_1$-$C_6$ alkoxy group,
  halogen atom, or
  a group —$NR^{11}R^{12}$ (wherein $R^{11}$ is hydrogen atom or $C_1$-$C_6$ alkyl group, and $R^{12}$ is $C_1$-$C_6$ alkyl group having a phenyl group as the substituent, phenyl group, benzoyl group which may optionally have $C_1$-$C_6$ alkyl group as the substituent, $C_1$-$C_6$ acyl group which may optionally have $C_1$-$C_6$ alkoxycarbonyl group as the substituent, $C_1$-$C_6$ alkylsulfonyl group or phenylsulfonyl group); with the proviso that when $R^{10}$ is hydrogen atom, the group A does not represent hydrogen atom, carboxy-$C_1$-$C_6$ alkyl group, $C_1$-$C_6$ alkoxycarbonyl-$C_1$-$C_6$ alkyl group, $C_1$-$C_6$ alkyl group, carboxyl group, $C_1$-$C_6$ alkoxy group or halogen atom, and a salt thereof.

The compounds of the formulas (1) through (4) and the salts thereof according to the present invention are novel compounds undisclosed in literature. They have both antiinflammatory activity and an activity of inhibiting lipoxygenase. Therefore, they have therapeutic potential in treating diseased states such as acute inflammation and arthritis due to the reduction of inflammation and in treating diseased states such as asthma, bronchitis, psoriasis, cardiovascular insufficiency, and myocardial infarct due to the inhibition of the formation of lipoxygenase metabolites.

The compounds of the present invention exhibit such pharmaceutical activities for a prolonged period of time. They seldom cause formation of gastric ulcer and seldom cause nephropathy, and they are less toxic.

Of the compounds of the formulas (1) to (4) of the invention, preferred compounds are those selected from the group consisting of:

(1) a compound of the formula (1) wherein $R^1$ is a phenyl group having cyano or hydroxy-$C_1$-$C_6$ alkyl group as the substituent and $R^2$ and $R^3$ are the same or different and represent $C_1$-$C_6$ alkyl, (2) a compound of the formula (2) wherein $R^2$ and $R^3$ are the same or different and represent $C_1$-$C_6$ alkyl group and $R^4$ is a group

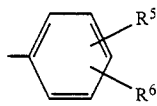

wherein $R^5$ is hydroxy-$C_1$-$C_6$ alkyl and $R^6$ is a halogen atom, (3) a compound of the formula (3) wherein $R^7$ is a fluorophenyl group, and (4) a compound of the formula (4) wherein $R^8$ and $R^9$ are the same or different and represent $C_1$-$C_6$ alkyl, $R^{10}$ is hydrogen atom or $C_1$-$C_6$ alkyl group, or $R^9$ and $R^{10}$, taken together with the phenyl group to which they are attached, form a fused ring of the formula

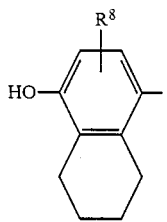

and A is a hydrogen atom, $C_2$-$C_6$ alkenyl group having a carboxyl or $C_1$-$C_6$ alkoxycarbonyl group as the substituent, $C_1$-$C_6$ alkoxy group, $C_1$-$C_6$ alkoxycarbonyl-$C_1$-$C_6$ alkyl group, $C_1$-$C_6$ alkyl group or halogen atom.

Typical examples of the above preferred compounds include the following:
2,6-di-tert-butyl-4-(4-chloro-2-hydroxymethylphenylamino)phenol
2,6-di-tert-butyl-4-(2-hydroxymethylphenylamino)phenol
2-(3,5-di-tert-butyl-4-hydroxyphenylamino)cinnamic acid
2,6-di-tert-butyl-4-(4-cyanophenylamino)phenol
2,6-di-tert-butyl-4-(4-fluorophenylamino)phenol
2,3,6-trimethyl-4-(4-methoxyphenylamino)phenol
2,3,6-trimethyl-4-(4-methoxycarbonylmethylphenylamino)phenol
2,3,6-trimethyl-4-(4-methylphenylamino)phenol
2,3,6-trimethyl-4-(4-chlorophenylamino)phenol
2-methyl-4-phenylamino-5,6,7,8-tetrahydronaphthol
2-methyl-4-(4-methoxycarbonylmethylphenylamino)-5,6,7,8-tetrahydronaphthol
2,3,6-trimethyl-4-phenylaminophenol
ethyl 3-(4-hydroxy-2,3,5-trimethylphenylamino)cinnamate The compounds which are analogues of the compounds of the formulas (1) through (4) are disclosed in U.S. Pat. No. 3787174, No. 3905761, No. 3953508, No. 4008043, No. 4008999, No. 4042627, No. 4054147, No. 4112229, No. 4170452, No. 4200432, No. 4222958, No. 4233241, No. 4496590, No. 4510139, No. 4515980, Japanese Unexamined Patent Publication No. 50-88040, Japanese Examined Patent Publication No. 59-27329, Izv. Akad. Nauk SSSR, Ser. Khim., 1971, 609, Zh. Obshch. Khim., 55, 648 (1985). However, these publications do not disclose the compounds of the formulas (1) to (4) and their pharmaceutical activities, particularly anti-inflammatory activity and lipoxygenase-inhibitory activity.

Therefore, the present invention also provides an anti-inflammatory composition and a composition for inhibiting lipoxygenase each comprising an effective amount of at least one of the compounds of the formulas (1) to (4) and the salts thereof in combination with a pharmaceutically acceptable carrier.

According to our investigation, it has been found that some of the compounds disclosed in the foregoing prior art publications also have the same pharmaceutical activities as the compounds of the formulas (1) to (4).

Therefore, the present invention provides a method for treating an inflammatory condition in a patient comprising administering to said patient an effective amount of at least one compound selected from the group consisting of:

(a) a compound of the formula

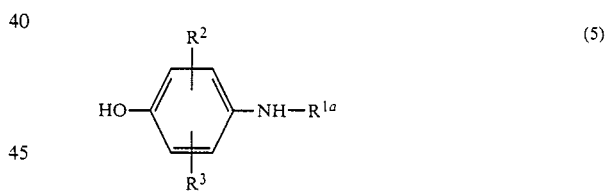

wherein $R^{1a}$ represents unsubstituted phenyl group or a phenyl group having 1-3 substituents selected from the class consisting of cyano group, carbamoyl group, nitro group, sulfamoyl group, hydroxy-$C_1$-$C_6$ alkyl group, $C_1$-$C_6$ alkoxycarbonyl-$C_1$-$C_6$ alkyl group, carboxy-$C_1$-$C_6$ alkyl group, $C_1$-$C_6$ haloalkyl group, $C_1$-$C_6$ acyl group, $C_1$-$C_6$ alkylthio group, phenylthio group, $C_1$-$C_6$ alkylsulfonyl group, amino group, $C_1$-$C_6$ alkoxy group, hydroxyl group, $C_1$-$C_6$ alkyl group and halogen atom, and $R^2$ and $R^3$ are the same or different and represent $C_1$-$C_6$ alkyl group and a salt thereof; and (b) a compound of the formula

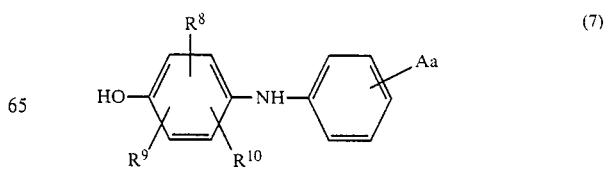

wherein $R^8$, $R^9$ and $R^{10}$ are as defined in the formula (4) above, and Aa represents:
a hydrogen atom,
$C_1$–$C_6$ alkylsulfonyl group,
$C_1$–$C_6$ alkoxycarbonyl group,
piperidinocarbonyl group,
phenyl-$C_1$–$C_6$ alkylcarbamoyl group,
$C_1$–$C_{12}$ alkylcarbamoyl group,
$C_3$–$C_8$ cycloalkylcarbamoyl group,
$C_2$–$C_6$ alkenyl group having a substituent selected from the class consisting of $C_1$–$C_6$ alkoxycarbonyl, carboxyl, $C_1$–$C_6$ acyl, $C_1$–$C_6$ alkylcarbamoyl and $C_3$–$C_8$ cycloalkylcarbamoyl groups,
$C_1$–$C_6$ alkyl group having a substituent selected from the class consisting of $C_3$–$C_8$ cycloalkylcarbamoyl, $C_1$–$C_6$ alkylcarbamoyl, phenyl-$C_1$–$C_6$ alkylcarbamoyl, piperidinocarbonyl, morpholinocarbonyl and hydrazinocarbonyl groups,
carboxy-$C_1$–$C_6$ alkyl group,
$C_1$–$C_6$ alkoxycarbonyl-$C_1$–$C_6$ alkyl group,
$C_1$–$C_6$ alkyl group,
carboxyl group,
$C_1$–$C_6$ alkoxy group,
halogen atom, or
a group $—NR^{11}R^{12a}$ (wherein $R^{11}$ is hydrogen atom or $C_1$–$C_6$ alkyl group, and $R^{12a}$ is $C_1$–$C_6$ alkyl group, $C_1$–$C_6$ alkyl group having a phenyl group as the substituent, phenyl group, benzoyl group which may optionally have $C_1$–$C_6$ alkyl group as the substituent, $C_1$–$C_6$ acyl group which may optionally have $C_1$–$C_6$ alkoxycarbonyl group as the substituent, $C_1$–$C_6$ alkylsufonyl group or phenylsulfonyl group); with the proviso that when $R^{10}$ is hydrogen atom, the group Aa does not represent hydrogen atom, carboxy-$C_1$–$C_6$ alkyl group, $C_1$–$C_6$ alkoxycarbonyl-$C_1$–$C_6$ alkyl group, $C_1$–$C_6$ alkyl group, carboxyl group, $C_1$–$C_6$ alkoxy group or halogen atom, and a salt thereof.

The present invention also provides a method for inhibiting lipoxygenase in a patient comprising administering to said patient as effective amount of at least one compound selected from the group consisting of:

(a) a compound of the formula

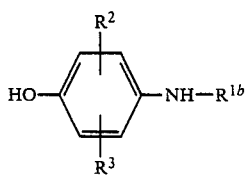

(6)

wherein $R^{1b}$ represents unsubstituted phenyl group or a phenyl group having 1–3 substituents selected from the class consisting of carboxyl group, cyano group, carbamoyl group, nitro group, sulfamoyl group, hydroxy-$C_1$–$C_6$ alkyl group, $C_1$–$C_6$ alkoxycarbonyl-$C_1$–$C_6$ alkyl group, carboxy-$C_1$–$C_6$ alkyl group, $C_1$–$C_6$ haloalkyl group, $C_1$–$C_6$ acyl group, $C_1$–$C_6$ alkylthio group, phenylthio group, $C_1$–$C_6$ alkylsulfonyl group, amino group, $C_1$–$C_6$ alkoxy group, hydroxyl group, $C_1$–$C_6$ alkyl group and halogen atom, and $R^2$ and $R^3$ each are the same or different and represent $C_1$–$C_6$ alkyl group and a salt thereof; and (b) a compound of the formula

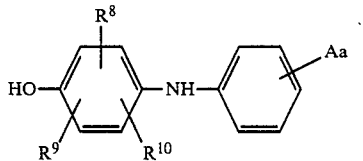

(7)

wherein $R^8$, $R^9$ and $R^{10}$ are as defined in the formula (4) above, and Aa represents:
a hydrogen atom,
$C_1$–$C_6$ alkylsulfonyl group,
$C_1$–$C_6$ alkoxycarbonyl group,
piperidinocarbonyl group,
phenyl-$C_1$–$C_6$ alkylcarbamoyl group,
$C_1$–$C_{12}$ alkylcarbamoyl group,
$C_3$–$C_8$ cycloalkylcarbamoyl group,
$C_2$–$C_6$ alkenyl group having a substituent selected from the class consisting of $C_1$–$C_6$ alkoxycarbonyl, carboxyl, $C_1$–$C_6$ acyl, $C_1$–$C_6$ alkylcarbamoyl and $C_3$–$C_8$ cycloalkylcarbamoyl groups,
$C_1$–$C_6$ alkyl group having a substituent selected from the class consisting of $C_3$–$C_8$ cycloalkylcarbamoyl, $C_1$–$C_6$ alkylcarbamoyl, phenyl-$C_1$–$C_6$ alkylcarbamoyl, piperidinocarbonyl, morpholinocarbonyl and hydrazinocarbonyl groups,
carboxy-$C_1$–$C_6$ alkyl group,
$C_1$–$C_6$ alkoxycarbonyl-$C_1$–$C_6$ alkyl group,
$C_1$–$C_6$ alkyl group,
carboxyl group,
$C_1$–$C_6$ alkoxy group,
halogen atom, or
a group $—NR^{11}R^{12a}$ (wherein $R^{11}$ is hydrogen atom or $C_1$–$C_6$ alkyl group, and $R^{12a}$ is $C_1$–$C_6$ alkyl group, $C_1$–$C_6$ alkyl group having a phenyl group as the substituent, phenyl group, benzoyl group which may optionally have $C_1$–$C_6$ alkyl group as the substituent, $C_1$–$C_6$ acyl group which may optionally have $C_1$–$C_6$ alkoxycarbonyl group as the substituent, $C_1$–$C_6$ alkylsulfonyl group or phenylsulfonyl group); with the proviso that when $R^{10}$ is hydrogen atom, the group Aa does not represent hydrogen atom, carboxy-$C_1$–$C_6$ alkyl group, $C_1$–$C_6$ alkoxycarbonyl-$C_1$–$C_6$ alkyl group, $C_1$–$C_6$ alkyl group, carboxyl group, $C_1$–$C_6$ alkoxy group or halogen atom, and a salt thereof.

In a method for treating an inflammatory condition according to the present invention, it is preferable to use a compound selected from the group consisting of:

(a) a compound of the formula (5) wherein $R^{1a}$ is unsubstituted phenyl group, phenyl group having a halogen atom and hydroxy-$C_1$–$C_6$ alkyl group as the substituent, phenyl group having hydroxy-$C_1$–$C_6$ alkyl group as the substituent, cyanophenyl group or halophenyl group and $R^2$ and $R^3$ are the same or different and each represent $C_1$–$C_6$ alkyl group, and (b) a compound of the formula (7) wherein $R^8$, $R^9$ and $R^{10}$ are as defined in the formula (7) and Aa is $C_2$–$C_6$ alkenyl group having carboxyl group as the substituent.

Typical examples of the foregoing preferred compounds of the formulas (5) and (7) include the following compounds.

2,6-di-tert-butyl-4-(4-chloro-2-hydroxymethylphenylamino)phenol
2,6-di-tert-butyl-4-(2-hydroxymethylphenylamino)-phenol
2-(3,5-di-tert-butyl-4-hydroxyphenylamino)cinnamic acid 2,6-di-tert-butyl-4-(4-cyanophenylamino)phenol
2,6-di-tert-butyl-4-(4-fluorophenylamino)phenol
2,6-di-tert-butyl-4-phenylaminophenol In the method for inhibiting lipoxygenase according to the present invention, it is preferable to use a compound of the formula (7) wherein $R^8$, $R^9$ and $R^{10}$ are as defined in the formula (7) and Aa is hydrogen, $C_1$–$C_6$ alkoxy, $C_1$–$C_6$ alkoxycarbonyl-$C_1$–$C_6$ alkyl, $C_1$–$C_6$ alkyl, halogen or $C_2$–$C_6$ alkenyl having $C_1$–$C_6$ alkoxycarbonyl group as the substituent.

Typical examples of the above preferred compounds of the formula (7) include the following compounds.
2,3,6-trimethyl-4-(4-methoxyphenylamino)phenol
2,3,6-trimethyl-4-(4-methoxycarbonylmethylphenylamino)phenol
2,3,6-trimethyl-4-(4-methylphenylamino)phenol
2,3,6-trimethyl-4-(4-chlorophenylamino)phenol
2-methyl-4-phenylamino-5,6,7,8-tetrahydronaphthol
2-methyl-4-(4-methoxycarbonylmethylphenylamino)5,6,7,8-tetrahydronaphthol
2,3,6-trimethyl-4-phenylaminophenol
ethyl 3-(4-hydroxy-2,3,5-trimethylphenylamino)cinnamate Throughout the specification and claims, the terms listed below have the following meanings.

Examples of $C_1$–$C_6$ alkyl groups are straight- or branched-chain alkyl groups such as methyl, ethyl, propyl, isopropyl, butyl, isobutyl, tert-butyl, pentyl, hexyl and the like.

Examples of phenyl-$C_1$–$C_6$ alkyl groups are benzyl, 1-phenylethyl, 2-phenylethyl, 3-phenylpropyl, 2-phenyl-1-methylethyl, 4-phenylbutyl, 2-phenyl-1,1-dimethylethyl, 5-phenylpentyl, 6-phenylhexyl and the like.

Examples of $C_1$–$C_6$ alkoxycarbonyl groups are methoxycarbonyl, ethoxycarbonyl, propoxycarbonyl isopropoxycarbonyl, butoxycarbonyl, tert-butoxycarbonyl, pentyloxycarbonyl, hexyloxycarbonyl and the like.

Examples of $C_1$–$C_6$ acyl groups are acetyl, propionyl, butyryl, isobutyryl, valeryl, isovaleryl, pivaloyl, hexanoyl and the like.

Examples of $C_1$–$C_6$ alkylcarbamoyl groups are methylcarbamoyl, ethylcarbamoyl, propylcarbamoyl, isopropylcarbamoyl, butylcarbamoyl, tert-butylcarbamoyl, pentylcarbamoyl, hexylcarbamoyl and the like.

Examples of cycloalkylcarbamoyl groups are $C_3$–$C_8$ cycloalkylcarbamoyl groups such as cyclopropylcarbamoyl, cyclobutylcarbamoyl, cyclopentylcarbamoyl, cyclohexylcarbamoyl, cycloheptylcarbamoyl, cyclooctylcarbamoyl and the like.

Examples of alkylcarbamoyl groups include, in addition to the above-exemplified $C_1$–$C_6$ alkylcarbamoyl groups, $C_7$–$C_{12}$ alkylcarbamoyl groups, such as heptylcarbamoyl, octylcarbamoyl, nonylcarbamoyl, 2-methyloctylcarbamoyl, decanylcarbamoyl, undecanylcarbamoyl, dodecanylcarbamoyl and the like.

Examples of piperidinocarbonyl groups are 1-piperidinocarbonyl, 2-piperidinocarbonyl, 3-piperidinocarbonyl, 4-piperidinocarbonyl and the like.

Examples of phenyl-$C_1$–$C_6$ alkylcarbamoyl groups are benzylcarbamoyl, 1-phenylethylcarbamoyl, 2-phenylethylcarbamoyl, 3-phenylpropylcarbamoyl, 2-phenyl-1-methylethylcarbamoyl, 4-phenylbutylcarbamoyl, 2-phenyl-1,1-dimethylethylcarbamoyl, 5-phenylpentylcarbamoyl, 6-phenylhexylcarbamoyl and the like.

Examples of $C_2$–$C_6$ alkenyl groups are vinyl, allyl, isopropenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl and the like.

Examples of morpholinocarbonyl groups are 2-morpholinocarbonyl, 3-morpholinocarbonyl, 4-morpholinocarbonyl and the like.

Examples of benzoyl groups optionally having $C_1$–$C_6$ alkyl group as the substituent are benzoyl and 2-methylbenzoyl, 3-methylbenzoyl, 4-methylbenzoyl, 3-ethylbenzoyl, 4-propylbenzoyl, 4-butylbenzoyl, 3-pentylbenzoyl, 4-hexylbenzoyl and the like.

Examples of $C_1$–$C_6$ acyl groups optionally having $C_1$–$C_6$ alkoxycarbonyl group as the substituent include, in addition to the $C_1$–$C_6$ acyl exemplified above, methoxycarbonylacetyl, ethoxycarbonylacetyl, 3-(methoxycarbonyl)propionyl, 3-(ethoxycarbonyl)propionyl, 2-(methoxycarbonyl)propionyl and the like.

Examples of $C_1$–$C_6$ alkylsulfonyl groups are methylsulfonyl, ethylsulfonyl, propylsulfonyl, isopropylsulfonyl, butylsulfonyl, tert-butylsulfonyl, pentylsulfonyl, hexylsulfonyl and the like.

Examples of halogen atoms include fluorine, chlorine, bromine and iodine.

Examples of hydroxy-$C_1$–$C_6$ alkyl groups are hydroxymethyl, 1-hydroxyethyl, 2-hydroxyethyl, 1-hydroxypropyl, 2-hydroxypropyl, 3-hydroxypropyl, 2-hydroxy-1-methylethyl, 1-hydroxybutyl, 2-hydroxybutyl, 3-hydroxybutyl, 4-hydroxybutyl, 1-hydroxypentyl, 2-hydroxypentyl, 3-hydroxypentyl, 4-hydroxypentyl, 5-hydroxypentyl, 1-hydroxyhexyl, 2-hydroxyhexyl, 6-hydroxyhexyl and the like.

Examples of $C_1$–$C_6$ alkoxycarbonyl-$C_1$–$C_6$ alkyl groups are methoxycarbonylmethyl, ethoxycarbonylmethyl, propoxycarbonylmethyl, isopropylcarbonylmethyl, butoxycarbonylmethyl, pentyloxycarbonylmethyl, hexyloxycarbonylmethyl, 1-methoxycarbonylethyl, 2-methoxycarbonylethyl, 3-methoxycarbonylpropyl, 2-methoxycarbonylbutyl, 4-methoxycarbonylbutyl, 3-methoxycarbonylpentyl, 5-methoxycarbonylpentyl, 4-methoxycarbonylhexyl, 6-methoxycarbonylhexyl, 4-ethoxycarbonylbutyl, 3-(1-butoxy)carbonylpropyl, 6-(1-propoxy)carbonylhexyl and the like.

Examples of carboxy-$C_1$–$C_6$ alkyl groups are carboxymethyl, 1-carboxyethyl, 2-carboxyethyl, 2-carboxypropyl, 3-carboxypropyl, 2-carboxybutyl, 4-carboxybutyl, 3-carboxypentyl, 5-carboxypentyl, 3-carboxyhexyl, 5-carboxyhexyl, 6-carboxyhexyl and the like.

Examples of $C_1$–$C_6$ haloalkyl groups are fluoromethyl, difluoromethyl, trifluoromethyl, chloromethyl, dichloromethyl, trichloromethyl, bromomethyl, dibromomethyl, tribromomethyl, iodomethyl, diiodomethyl, triiodomethyl, 1-fluoroethyl, 2-fluoroethyl, 1,2-difluoroethyl, 2,2-difluoroethyl, 1,2-dichloroethyl, 2,2-dichloroethyl, 2-chloro-2-fluoroethyl, 2-bromoethyl, 2,2-dibromoethyl, 2,2,2-trifluoroethyl, 1,3-difluoropropyl, 3,3,3-trifluoropropyl, 3,3-dichloropropyl, 2,4-dibromobutyl, 4,4,4-tribromobutyl, 4,4-difluorobutyl, 3,5-dichloropentyl, 5,5-difluoropentyl, 5,5,5-trifluoropentyl, 6,6-dibromohexyl, 6,6,6-trifluorohexyl and the like.

Examples of $C_1$–$C_6$ alkylthio groups are methylthio, ethylthio, 1-propylthio, 2-propylthio, 1-butylthio, 2-butylthio, tert-butylthio, 1-pentylthio, 2-pentylthio, 3-pentylthio, 1-hexylthio, 2-hexylthio, 3-hexylthio and the like.

Examples of $C_1$–$C_6$ alkoxy groups are straight- or branched-chain alkoxy groups such as methoxy, ethoxy, propoxy, butoxy, tert-butoxy, pentyloxy, hexyloxy and the like.

Examples of tri($C_1$–$C_6$ alkoxy)phenyl groups are 3,4,5-trimethoxyphenyl, 2,4,6-trimethoxyphenyl, 2,3,5- trimethoxyphenyl, 3,4,5-triethoxyphenyl, 3,4-dimethoxy-5-ethoxyphenyl, 2,6-dimethoxy-4-ethoxyphenyl, 2,6-dimethoxy-4-tert-butoxyphenyl, 2,4,6-trihexyloxyphenyl and the like.

Examples of dihalophenyl groups are 2,6-dichlorophenyl, 2,6-dibromophenyl, 2,4-dichlorophenyl, 3,5-dichlorophenyl, 3,4-dibromophenyl, 2,4-difluorophenyl, 2-chloro-4-bromophenyl, 3-chloro-5-bromophenyl, 3-bromo-5-fluorophenyl and the like.

Examples of N,N-di($C_1$-$C_6$ alkyl)amino groups are N,N-dimethylamino, N,N-diethylamino, N,N-dipropylamino, N,N-dibutylamino, N,N-dipentylamino, N,N-dihexylamino, N-methyl-N-ethylamino, N-methyl-N-butylamino, N-methyl-N-hexylamino, N-ethyl-N-propylamino and the like.

Examples of phenyl groups having halogen atom and hydroxyl group as the substituent are 2-hydroxy-4-chlorophenyl, 2-hydroxy-5-chlorophenyl, 2-hydroxy-6-bromophenyl, 3-hydroxy-5-fluorophenyl, 4-hydroxy-2-chlorophenyl, 4-hydroxy-2-bromophenyl and the like.

Examples of phenyl groups having $C_1$-$C_6$ alkoxy and hydroxy groups as the substituent are 2-hydroxy-4-methoxyphenyl, 2-hydroxy-5-methoxyphenyl, 2-hydroxy-6-methoxyphenyl, 2-hydroxy-4-butoxyphenyl, 2-hydroxy-4-hexyloxyphenyl, 3-hydroxy-5-methoxyphenyl, 4-hydroxy-2-methoxyphenyl, 4-hydroxy-3-methoxyphenyl and the like.

Examples of the phenyl groups having 1–3 of the substituents exemplified above are as follows:

2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-iodophenyl, 3-iodophenyl, 4-iodophenyl, 2,4-difluorophenyl, 2,4-dichlorophenyl, 2,4,6-trifluorophenyl, 2,4,6-trichlorophenyl, 2-hydroxyphenyl, 3-hydroxyphenyl, 4-hydroxyphenyl, 2,4-dihydroxyphenyl, 2,4,6-trihydroxyphenyl, 2-trifluoromethylphenyl, 3-trifluoromethylphenyl, 4-trifluoromethylphenyl, 3,5-di(trifluoromethyl)phenyl, 2-carboxymethylphenyl, 3-carboxymethylphenyl, 4-carboxymethylphenyl, 2,4-dicarboxymethylphenyl, 2-ethoxycarbonylmethylphenyl, 3-ethoxycarbonylmethylphenyl, 4-ethoxycarbonylmethylphenyl, 2,4-diethoxycarbonylmethylphenyl, 2,4,6-triethoxycarbonylmethylphenyl, 2-methoxyphenyl, 3-methoxyphenyl, 4-methoxyphenyl, 2,4-dimethoxyphenyl, 2,4,6-trimethoxyphenyl, 3,4,5-trimethoxyphenyl, 2-ethoxyphenyl, 4-ethoxyphenyl, 2,4-diethoxyphenyl, 2,4,6-triethoxyphenyl, 2,4,6-tricarboxymethylphenyl, 2-acetylphenyl, 3-acetylphenyl, 4-acetylphenyl, 2,4-diacetylphenyl, 2-(1-carboxyethyl)phenyl, 3-(1-carboxyethyl)phenyl, 4-(1-carboxyethyl)phenyl, 2,4-di(1-carboxyethyl)phenyl, 2-(2-carboxyethyl)phenyl, 3-(2-carboxyethyl)phenyl, 4-(2-carboxyethyl)phenyl, 2,4-di(2-carboxyethyl)phenyl, 2-methylthiophenyl, 3-methylthiophenyl, 4-methylthiophenyl, 2,4-dimethylthiophenyl, 2,4,6-trimethylthiophenyl, 3,4,5-trimethylthiophenyl, 2-aminophenyl, 3-aminophenyl, 4-aminophenyl, 2,4-diaminophenyl, 2,4,6-triaminophenyl, 2-phenylthiophenyl, 3-phenylthiophenyl, 4-phenylthiophenyl, 2-(1-pentylthio)phenyl, 3-(1-pentylthio)phenyl, 4-(1-pentylthio)phenyl, 2,4-di(1-pentylthio)phenyl, 2-methylphenyl, 3-methylphenyl, 4-methylphenyl, 2,4-dimethylphenyl, 2,4,6-trimethylphenyl, 2-(1-butyl)phenyl, 3-(1-butyl)phenyl, 4-(1-butyl)phenyl, 2,4-di(1-butyl)phenyl, 2,4,6-tri(1-butyl)phenyl, 3-chloro-2-hydroxyphenyl, 4-chloro-2-hydroxyphenyl, 5-chloro-2-hydroxyphenyl, 6-chloro-2-hydroxyphenyl, 4-chloro-3-hydroxyphenyl, 5-chloro-3-hydroxyphenyl, 2-(3-carboxypropyl)phenyl, 3-(3-carboxypropyl)phenyl, 4-(3-carboxypropyl)phenyl, 2,4-di(3-carboxypropyl)phenyl, 2-hydroxy-4-carboxymethylphenyl, 2-hydroxy-5-carboxymethylphenyl, 2-hydroxy-6-carboxymethylphenyl, 3-hydroxy-5-carboxymethylphenyl, 2-carboxyphenyl, 3-carboxyphenyl, 4-carboxyphenyl, 3,5-dicarboxyphenyl, 2-chloro-6-carboxyphenyl, 4-chloro-6-carboxyphenyl, 2-chloro-4-carboxyphenyl, 3-chloro-5-carboxyphenyl, 2-cyanophenyl, 3-cyanophenyl, 4-cyanophenyl, 3,5-dicyanophenyl, 2,4,6-tricyanophenyl, 4-methyl-2-carboxyphenyl, 6-methyl-2-carboxyphenyl, 2-methyl-4-carboxyphenyl, 3-methyl-5-carboxyphenyl, 4-hydroxy-3-carboxyphenyl, 4-hydroxy-2-carboxyphenyl, 6-hydroxy-2-carboxyphenyl, 2-hydroxymethylphenyl, 3-hydroxymethylphenyl, 4-hydroxymethylphenyl, 2,6-di(hydroxymethyl)phenyl, 2,4,6-tri(hydroxymethyl)phenyl, 2-(2-hydroxyethyl)phenyl, 3-(2-hydroxyethyl)phenyl, 4-(2-hydroxyethyl)phenyl, 3,5-di(2-hydroxyethyl)phenyl, 2-(1-hydroxyethyl)phenyl, 3-(1-hydroxyethyl)phenyl, 4-(1-hydroxyethyl)phenyl, 2,4-di(1-hydroxyethyl)phenyl, 2,4,6-tri(1-hydroxyethyl)phenyl, 2-(3-hydroxypropyl)phenyl, 3-(3-hydroxypropyl)phenyl, 4-(3-hydroxypropyl)phenyl, 3,5-di(3-hydroxypropyl)phenyl, 2,4-di(3-hydroxypropyl)phenyl, 2-(4-hydroxybutyl)phenyl, 3-(4-hydroxybutyl)phenyl, 4-(4-hydroxybutyl)phenyl, 2,4-di(4-hydroxybutyl)phenyl, 2-(1-hydroxyisopropyl)phenyl, 3-(1-hydroxyisopropyl)phenyl, 4-(1-hydroxyisopropyl)phenyl, 2,6-di(1-hydroxyisopropyl)phenyl, 2-chloro-6-hydroxymethylphenyl, 3-chloro-6-hydroxymethylphenyl, 4-chloro-6-hydroxymethylphenyl, 2-chloro-4-hydroxymethylphenyl, 2-chloro-5-hydroxymethylphenyl, 2-hydroxy-4-(2-hydroxyethyl)phenyl, 2-hydroxy-5-(2-hydroxyethyl)phenyl, 2-hydroxy-6-(2-hydroxyethyl)phenyl, 3-hydroxy-5-(2-hydroxyethyl)phenyl, 6-methyl-2-(hydroxymethyl)phenyl, 5-methyl-2-(hydroxymethyl)phenyl, 4-methyl-2-(hydroxymethyl)phenyl, 2-methyl-4-(hydroxymethyl)phenyl and the like.

The phenol derivatives of the invention can be prepared by various processes, as illustrated in the following reaction schemes.

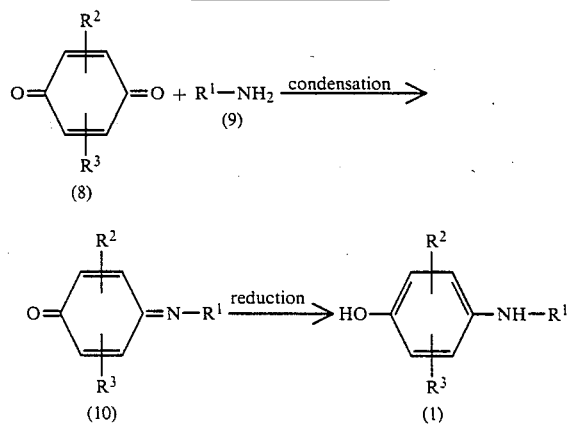

<Reaction scheme-1>

In the foregoing formulas, $R^1$, $R^2$ and $R^3$ are as defined above.

The condensation reaction as shown in Reaction scheme-1 is conducted by reacting the benzoquinone derivative (8) with the aniline derivative (9) which acts not only as a reactant but also as an acid binder in an inert organic solvent in the presence of a halide-type Lewis acid at a temperature of between room temperature and about 120° C. Examples of the inert organic solvents are 1,2-dichloroethane, chloroform, toluene, benzene and the like. Examples of the halide-type Lewis acids are aluminum chloride, ferric chloride, titanium tetrachloride, stannic chloride, zinc chloride and the like. An inert organic base such as pyridine, triethylamine or the like may optionally be added to the reaction system as an acid binder. There is no specific restriction on the proportions of the benzoquinone derivative (8) an aniline derivative (9). However, it is preferable to use about 1 to about 10 moles, preferably about 1 to about 3 moles, of the aniline derivative (9) per mole of the beznoquinone derivative (8).

The foregoing reaction in which titanium tetrachloride is used can be conducted, for example, according to the method disclosed by H. Weingarten et al. in J. Org. Chem., 32, 3246 (1967).

The above condensation reaction can also be conducted by a known method such as those described by A Reiker and H. Kessler in Tetrahedron, 23, 3723 (1967) or by J. Figueras et al. in J. Org. Chem., 36, 3497 (1971). Stated specifically, the condensation reaction can be carried out using 1 to 5 moles of the compound (9) per mole of the compound (8) at a temperature of about 30° to about 200° C. in the presence of a catalyst, such as acetic acid, boron trifluoride-ethyl ether complex (($C_2H_5)_2O.BF_3$) or the like, without using any solvent or in a suitalbe solvent such as tetrahydrofuran (THF), ether, dioxane, chloroform, 1,2-dichloroethane, benzene, toluene or xylene.

The compound (10) obtained by the reaction can be subjected to the subsequent reduction reaction without being isolated from the reaction mixture, or of course, as isolated therefrom.

The reduction reaction can be carried out by a usual method, for example, by placing the reaction product into THF and adding to the mixture 2 to 50 moles of sodium hydrosulfite ($Na_2S_2O_4$) in the form of an aqueous solution per mole of the product. Depending on the kind of substituent of group $R^1$ included in the compound (10), the reduction reaction can alternatively be conducted, for example, by using zinc powder in acetic acid, by catalytically hydrogenating the compound (10) in a solvent, such as ethyl acetate, alcohol, THF or water, in the presence of a catalyst such as palladium-carbon or platinum oxide, or by using sodium borohydride ($NaBH_4$) in a mixture of THF and water.

Further the compounds (1) of the present invention wherein $R^1$ is a phenyl group having hydroxy-$C_1$-$C_6$ alkyl group can be obtained also by reducing the compound (1) wherein $R^1$ is a phenyl group having carboxy-$C_1$-$C_6$ alkyl group or a phenyl group having $C_1$-$C_6$ alkoxycarbonyl-$C_1$-$C_6$ alkyl group with about 1 to about 7 moles of lithium aluminum hydride ($LiAlH_4$) per mole of the latter in a suitable solvent such as ether or THF, or alternatively by reducing the compound (1) wherein $R^1$ is a phenyl group having $C_1$-$C_6$ acyl group with about 1.5 to about 5 moles of $NaBH_4$ per mole thereof in a suitable solvent such as methanol, ethanol, isopropanol or a mixture thereof with THF, dioxane or the like.

The compounds of the present invention of the formulas (2) to (7) can be prepared also similarly according to Reaction scheme-1 using suitable starting materials as will be described below.

The compound of the formula (2) of the invention can be prepared using an amine represented by the formula $$R^4\text{—}NH_2 \qquad (11)$$

wherein $R^4$ is as defined above, in place of the aniline derivative of the formula (9).

The compound of the formula (3) can be prepared using 2,6-di-tert-butyl-1,4-benzoquinone of the formula

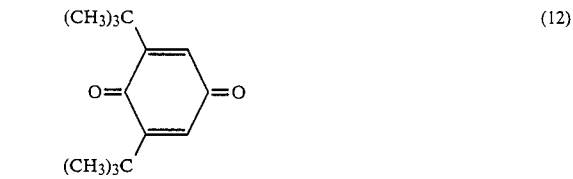
(12)

as the benzoquinone derivative of the formula (8) and also using an amine of the formula $$R^7\text{—}NH_2 \qquad (13)$$

wherein $R^7$ is as defined above, in place of the aniline derivative of the formula (9).

The compound of the formula (4) can be prepared using a compound of the formula

(14)

wherein $R^8$, $R^9$ and $R^{10}$ are as defined above, in place of the benzoquinone derivative (8) and further using an amine of the formula

(15)

wherein A is as defined above, in place of the aniline derivative (9).

The foregoing known compounds which are found to have pharmacological activities such as anti-inflammatory activity of lipoxygenase inhibitory activity by the present inventors can be prepared by known methods, while the compounds of the formulas (5), (6) and (7) including these known compounds can also be prepared similarly by the process of Reaction scheme-1 as will be described below.

The compounds of the formula (5) can be prepared using, in place of the aniline derivative (9), an amine of the formula $$R^{1a}\text{—}NH_2 \qquad (16)$$

wherein $R^{1a}$ is as defined above, and the compound of the formula (6) can be prepared using an amine of the formula $$R^{1b}\text{—}NH_2 \qquad (17)$$

wherein $R^{1b}$ is as defined above. Similarly, the compound of the formula (7) can be prepared using a compound of the formula (14) in place of the benzoquinone derivative (8) and further using an amine of the formula

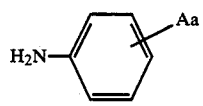
(18)

wherein Aa is as defined above in place of the aniline derivative (9).

The benzoquinone derivatives (8), (12) and (14) to be used as the starting materials are known or can be prepared by known methods, while the other starting materials, i.e., the aniline derivatives (9) or amines (11), (13), (15), (16), (17) and (18) are also known or can be prepared by known methods.

<Reaction Scheme-2>

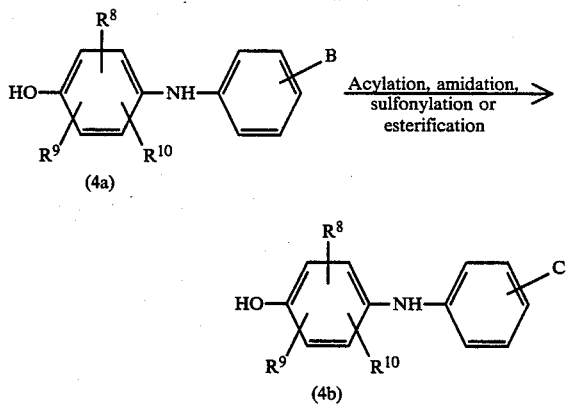

wherein $R^8$, $R^9$ and $R^{10}$ are as defined above, B is —NHR$^{11}$ (wherein $R^{11}$ is as defined above), carboxy-$C_1$-$C_6$ alkyl, carboxyl or carboxy-substituted $C_2$-$C_6$ alkenyl, and C is —NR$^{11}$R$^{12b}$ (wherein $R^{11}$ is as defined above, and $R^{12b}$ is benzoyl optionally having $C_1$-$C_6$ alkyl as the substituent, $C_1$-$C_6$ acyl optionally having $C_1$-$C_6$ alkoxycarbonyl as the substituent, $C_1$-$C_6$ alkylsulfonyl or phenylsulfonyl), $C_1$-$C_6$ alkoxycarbonyl, phenyl-$C_1$-$C_6$ alkylcarbamoyl, $C_1$-$C_{12}$ alkylcarbamoyl, $C_3$-$C_8$ cycloalkylcarbamoyl, $C_2$-$C_6$ alkenyl having a substituent selected from the group consisting of $C_1$-$C_6$ alkylcarbamoyl, $C_1$-$C_6$ alkoxycarbonyl and $C_3$-$C_8$ cycloalkylcarbamoyl, or $C_1$-$C_6$ alkyl having a substituent selected from the group consisting of $C_3$-$C_8$ cycloalkylcarbamoyl, $C_1$-$C_6$ alkylcarbamoyl, $C_1$-$C_6$ alkoxycarbonyl, phenyl-$C_1$-$C_6$ alkylcarbamoyl, piperidinocarbonyl, morpholinocarbonyl and hydrazinocarbonyl, provided that C is not $C_1$-$C_6$ alkoxycarbonyl-$C_1$-$C_6$ alkyl when $R^{10}$ is a hydrogen atom.

According to Reaction Scheme-2, the compound (4a), when acylated, amidated, sulfonylated or esterified, gives a compound (4b).

The compound (4a) is acylated or sulfonylated when the group B therein is amino. The acylation provides a compound of the formula (4b) wherein the group C is —NR$^{11}$R$^{12b}$ (wherein $R^{11}$ is as defined above, and $R^{12b}$ is benzoyl optionally having $C_1$-$C_6$ alkyl as the substituent or $C_1$-$C_6$ acyl optionally having $C_1$-$C_6$ alkoxycarbonyl as the substituent). The sulfonylation affords a compound of the formula (4b) wherein the group C is —NR$^{11}$R$^{12b}$ (wherein $R^{11}$ is as defined above, and $R^{12b}$ is $C_1$-$C_6$ alkylsulfonyl or phenylsulfonyl). The acylation and sulfonylation reactions are conducted in the following manner.

The acylation reaction is conducted in an inert solvent using a suitable acylating agent. Examples of useful acylating agents are $C_1$-$C_6$ acyl halides such as acetyl chloride, acetyl bromide, propionyl chloride, butyryl chloride, isobutyryl chloride, valeryl chloride, isovaleryl chloride, pivaloyl chloride and heptanoyl chloride; $C_1$-$C_6$ alkoxycarbonyl-$C_1$-$C_6$ acyl halides such as monoethylmalonic acid chloride, monomethylmalonic acid chloride, monomethylsuccinic acid chloride, monopropylglutaric acid chloride, monoethyladipic acid chloride and monomethylsuberic acid chlorde; benzoyl chloride optionally having $C_1$-$C_6$ alkyl as the substituent; etc. Examples of useful inert solvents are THF, diethyl ether, chloroform, dichloromethane, N,N-dimethylformamide (DMF), N,N-dimethylacetamide (DMA) and the like. The acylation reaction proceeds favorably at a temperature generally of about $-20°$ to 30° C. in the presence of a suitable base such as triethylamine, pyridine or collidine. While the amount of the acylating agent to be used is suitably determinable, it is usually about 1 to about 3 moles, preferably about 1 to about 1.1 moles, per mole of the starting compound.

The sulfonylation reaction can be carried out in the same manner as the acylation reaction in an inert organic solvent in the presence of a base using a suitable sulfonylating agent. Examples of useful sulfonylating agents are $C_1$-$C_6$ alkane sulfonyl halides such as methanesulfonyl chloride, ethanesulfonyl chloride, butanesulfonyl chloride and hexanesulfonyl chloride, benzenesulfonyl halides such as benzenesulfonyl chloride and benzene-sulfonyl bromide, etc.

The compound (4a) is amidated according to Reaction Scheme-2 when the group B therein is carboxyl, carboxy-$C_1$-$C_6$ alkyl or carboxy-$C_2$-$C_6$ alkenyl. When the group B is carboxyl, the amidation reaction gives a compound of the formula (4b) wherein the group C is phenyl-$C_1$-$C_6$ alkylcarbamoyl, $C_1$-$C_{12}$ alkylcarbamoyl, or $C_3$-$C_8$ cycloalkylcarbamoyl. When the group B is carboxy-$C_1$-$C_6$ alkyl, the reaction affords a compound of the formula (4b) wherein the group C is $C_1$-$C_6$ alkyl having a substituent selected from the group consisting of $C_3$-$C_8$ cycloalkylcarbamoyl, $C_1$-$C_6$ alkylcarbamoyl, phenyl-$C_1$-$C_6$ alkylcarbamoyl, piperidinocarbonyl, morpholinocarbonyl and hydrazinocarbonyl. When the group B is carboxy-$C_2$-$C_6$ alkenyl, the reaction gives a compound of the formula (4b) wherein the group C is $C_2$-$C_6$ alkenyl having $C_1$-$C_6$ alkylcarbamonyl or $C_3$-$C_8$ cycloalkylcarbamoyl substituent.

The amidation reaction can be carried out by a usual amide bond-forming reaction, for example, by the acid halide method, mixed anhydride method, activated ester method, N,N'-dicyclohexylcarbodiimide (DCC) method, azide method, diethyl phosphorocyanidate (DEPC) method or the like. Described in greater detail, DEPC method is practiced in a suitable solvent such as DMF, THF or ethyl acetate, using per mole of the compound (4a) about 1 to about 1.5 moles of a corresponding amine, such as $C_1$-$C_{12}$ alkylamine, phenyl-$C_1$-$C_6$ alkylamine, $C_3$-$C_8$ cycloalkylamine, hydrazine, morpholine or piperidine, about 1 to about 1.2 moles of DEPC and about 1 to about 5 moles of an organic amine such as triethylamine or pyridine. This reaction can be conducted usually at about 0° to about 30° C. with stirring for about 2 to about 20 hours.

The compound (4b) wherein the group C is $C_1$–$C_6$ alkyl having hydrazinocarbonyl as the substituent can be prepared alternatively by reacting a hydrazine hydrate with a compound (4a) wherein the group B is $C_1$–$C_6$ alkoxycarbonyl-$C_1$–$C_6$ alkyl. More specifically, this reaction is conducted usually in an alcohol solvent such as ethanol, methanol or tert-butanol with use of about 50 to about 300 moles of a hydrazine hydrate per mole of the compound (4a), by heating the mixture at the boiling point of the solvent for about 1 to about 20 hours.

The compound (4a) is esterified according to Reaction Scheme-2 when the group B is carboxyl, carboxy-$C_1$–$C_6$ alkyl or carboxy-$C_2$–$C_6$ alkenyl. The esterification reaction gives a compound of the formula (4b) wherein the group C is $C_1$–$C_6$ alkoxycarbonyl when the group B is carboxyl, or a compound of the formula (4b) wherein the group C is $C_1$–$C_6$ alkyl having $C_1$–$C_6$ alkoxycarbonyl as the substituent when the group B is carboxy-$C_1$–$C_6$ alkyl (provided that $R^{10}$ is not hydrogen). When the group B is carboxy-$C_2$–$C_6$ alkenyl, the reaction affords a compound of the formula (4b) wherein the group C is $C_2$–$C_6$ alkenyl having $C_1$–$C_6$ alkoxycarbonyl as the substituent.

The esterification reaction can be conducted by a usual method, for example, by reacting the compound (4a) with a $C_1$–$C_6$ alcohol with heating in the presence of an acid catalyst such as hydrochloric acid, sulfuric acid, p-toluenesulfonic acid, $(C_2H_5)_2O.BF_3$, or by reacting the compound (4a) with a $C_1$–$C_6$ alkyl halide in an amount of about 1 to about 10 moles per mole of the compound (4a) in an inert solvent, such as DMF, hexamethylphosphoramide (HMPA), dimethyl sulfoxide (DMSO), pyridine, chloroform, dichloromethane, THF, ethyl acetate, benzene or toluene, in the presence of about 1 to about 10 moles of a basic compound per mole of the compound (4a), examples of such basic compounds being pyridine, triethylamine, sodium hydrogen carbonate, potassium hydrogen carbonate, sodium carbonate, potassium carbonate, sodium acetate and potassium acetate.

The compound of the formula (4a) wherein the group B is carboxyl, —$NHR^{11}$ or carboxy-$C_1$–$C_6$ alkyl can be prepared substantially according to the process represented by Reaction Scheme-1.

<Reaction Scheme-3>

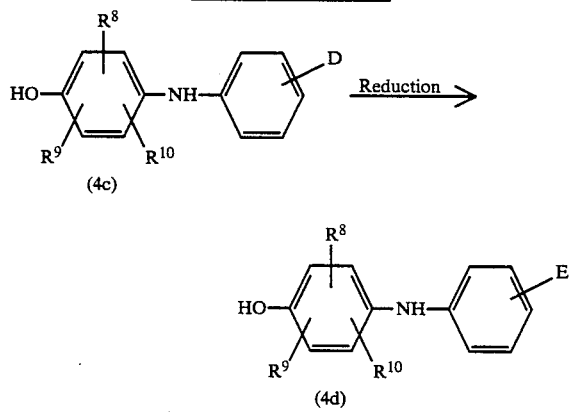

(4c)

(4d)

wherein $R^8$, $R^9$ and $R^{10}$ are as defined above, D is —$NR^{11}R^{12c}$ (wherein $R^{11}$ is as defined above, and $R^{12c}$ is $C_1$–$C_6$ acyl or benzoyl), and E is —$NR^{11}R^{12d}$ (wherein $R^{11}$ is as defined above, and $R^{12d}$ is $C_1$–$C_6$ alkyl or benzyl).

According to the process of Reaction Scheme-3, a compound (4c) is reduced to a compound (4d). This reduction reaction can be conducted favorably using $LiAlH_4$ usually in an amount of about 1 to about 10 moles per mole of the compound (4c) in an inert solvent such as diethyl ether or THF. Generally, the reaction proceeds under the temperature condition of about 0° C. to boiling point of the solvent.

The compounds of the formulas (1), (2) and (4) having carboxy-$C_1$–$C_6$ alkyl as a substituent on the phenyl ring, and the compounds of the formulas (3) and (4) similarly having carboxyl,

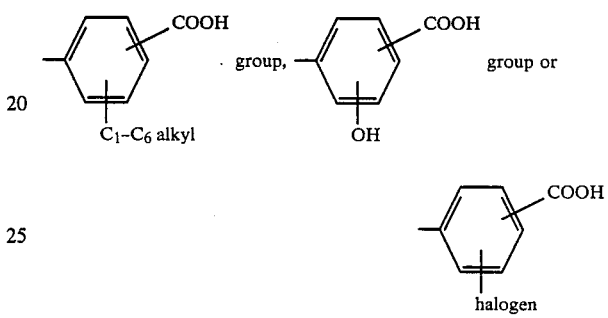

group can be prepared from suitable corresponding ester compounds, for example, from those having $C_1$–$C_6$ alkoxycarbonyl-$C_1$–$C_6$ alkyl, $C_1$–$C_6$ alkoxycarbonyl or like group on the phenyl ring, by subjecting the compound to a hydrolysis reaction. The hydrolysis reaction can be conducted under widely varying conditions which are commonly employed for hydrolysis, for example, substantially according to the method of Eliel et al. (Organic Synthesis, Vol. IV, p. 169, 1963)). More specifically, the desired compound having carboxy-$C_1$–$C_6$ alkyl or carboxyl as a substituent on the phenyl ring can be obtained by reacting a suitable acid, such as hydrochloric acid or hydrobromic acid, with the ester compound serving as the starting material in a suitable solvent, such as acetic acid, or without using any solvent, at room temperature to about 120° C. It is desirable to use the acid usually in a catalytic amount to an amount of about 10 moles per mole of the ester compound, although the amount is not limited specifically.

The compounds of the present invention obtained by the reactions represented by the foregoing schemes can be easily isolated and purified by a conventional separating method, such as solvent extraction, recrystallization or column chromatography.

The compound of the present invention thus obtained is subjected to an addition reaction with a suitable acid compound in the usual manner, whereby the compound can be easily converted to a pharmaceutically acceptable acid addition salt, which has the same pharmacological activity as the present compound in a free state. The present invention includes such acid addition salts. Examples of acid compounds useful for forming these acid addition salts are inorganic acids such as hydrochloric acid, sulfuric acid, phosphoric acid and hydrobromic acid, and organic acids such as oxalic acid, maleic acid, fumaric acid, malic acid, tartaric acid, citric acid, benzoic acid and benzenesulfonic acid.

Further, the present compounds which have a free carboxyl group can be converted by a conventional method to an alkali metal salt such as sodium salt and potassium salt, alkaline earth metal such as calcium salt and magnesium salt or other salts such as copper salt. These salts have the same pharmacological activities as the compound of the invention in a free state, and therefore are included in the present invention.

The desired products of the present invention are usually administered to mammals including humans in the form of generally acceptable pharmaceutical compositions which are prepared by using diluents and excipients such as filters, bulking agents, binders, wetting agents, disintegrating agents, surfactants, lubricants and the like. Administration unit forms of these pharmaceutical compositions of the present invention can be varied and selected so as to meet various therapeutical purposes. Typical forms of the pharmaceutical compositions can be exemplified such as tablets, pills, powders, liquids, suspensions, emulsions, granules, capsules, suppositories, injections (liquids, suspensions and others), ointments and the like.

In shaping into the form of tablets, those known as the carriers in this field can widely be applied for example, excipients such as lactose, purified sugar, sodium chloride, glucose, urea, starch, calcium carbonate, kaolin, crystalline cellulose, silicic acid and others; binders such as water, ethanol, propanol, simple syrup, a glucose solution, starch solution, gelatin solution, carboxymethyl cellulose, shellac, methyl cellulose, potassium phosphate, polyvinylpyrrolidone and others; disintegrating agents such as dried starch, sodium alginate, agar-agar powder, laminaran powder, sodium hydrogen carbonate, calcium carbonate, a fatty acid ester of polyoxyethylene sorbitan, sodium laurylsulfate, monoglyceride of stearic acid, starch, lactose and others; disintegration inhibitors such as purified sugar, stearin, cacao butter, hydrogenated oils and others; absorption accelerators such as quaternary ammonium base, sodium laurylsulfate and others; wetting agents such as glycerin, starch and others, adsorption accelerators such as starch, lactose, kaolin, bentonite, colloidal silicic acid and others; and lubricants such as purified talc powder, stearic acid salts, boric acid powder, polyethylene glycol and others can be examplified. If necessary, the tablets can further be coated with usual coating film to make them into coated tablets, for example sugar-coated tablets, gelatin film-coated tablets, enteric film-coated tablets, film-coated tablets, or double-layered tablets, multiple-layered tablets and others. In shaping into the form of pills, those known as the carriers in this field can widely be applied for example, excipients such as glucose, lactose, starch, cacao butter, hydrogenated vegetable oils, kaolin, talc and others; binders such as powdered gum arabi, powdered tragacanth gum, gelatin, ethanol and others; disintegrating agent such as laminaran, agar-agar powder and others. In shaping into the form of suppositories, those known in this field can widely be applied for example, polyethylene glycol, cacao butter, a higher alcohol, an ester of a higher alcohol, gelatin, semi-synthesized glyceride and others. Capsules are prepared in a conventional manner by admixing, the compound of the invention with the foregoing various carrier and encapsulating the mixture into hard-gelatin capsules, soft-gelatin capsules, etc. In case of preparing injections, solutions, emulsions and suspensions being prepared are sterilized, and they are preferably isotonic to the blood. In preparing into the form of solutions, emulsions and suspensions, those known as the diluents in this field can widely be applied, for example water, ethanol, propylene glycol, ethoxylated isostearyl alcohol, polyoxylated isostearyl alcohol, a polyoxyethylene sorbitan fatty acid ester and others. In case of preparing isotonic solutions, sufficient amount of sodium chloride, glucose or glycerin may be added to make the solution to be isotonic to the blood. The pharmaceutical compositions for injection preparation may further contain usual dissolving agents, buffer solutions, analgesic agents or the like if necessary. The pharmaceutical composition of the present invention may also contain coloring agents, preservatives, perfumes, seasoning agents, sweetening agents and others, as well as contain other medicines, if necessary. In shaping into the form of pastes, creams and gels, diluents such as white vaseline, paraffins, glycerine, cellulose derivatives, polyethylene glycols, silicones, bentonite and the like can be used.

The amount of the desired product according to the present invention to be contained as the active ingredient in the pharmaceutical composition is not specifically restricted and can be selected from a wide range, generally 1 to 70% by weight, may be used.

Administration method of the above-mentioned pharmaceutical composition is not specifically restricted and can be administered through a suitable method for the respective types of administration forms, depending upon age of the patient, distinction of the sex and other conditions, conditions of the patient and others. For example, tablets, pills, liquids, suspensions, emulsions, granules and capsules are administered orally; injections are administered intraveneously singly or as a mixture with usual injectable transfusions such as glucose solution, an amino acids solutions, and others; and if necessary the injections are administered singly intramuscularly, intracutaneously, subcutaneously or intraperitoneally; and the suppositories are administered into rectum.

The dosage of the desired products of the present invention may suitably be selected depending upon the method for administration, age of the patient, distinction of sex and other conditions, and conditions of the symptoms, and generally the pharmaceutical composition of the invention can be administered in an amount of about 0.5 to about 500 mg/kg of the body weight/day, calculated as the compound of the invention (active ingredient), in 2 to 4 divided doses.

The present invention will be described in greater detail with reference to examples.

EXAMPLE 1

Preparation of 2,6-di-tert-butyl-4-(4-fluorophenylamino)phenol

A 2.2 g quantity of 2,6-di-tert-butyl-1,4-benzoquinone and 3.3 g of p-fluoroaniline were dissolved in 60 ml of THF, and 0.3 ml of $(C_2H_5)_2O.BF_3$ was added to the solution. The solution was refluxed for 6 hours. After cooling, 50 ml of water and then a solution of 20 g of $Na_2S_2O_4$ in 150 ml of water were added to the red reaction mixture at room temperature, and the mixture was stirred for about 15 minutes until a decoloration took place. Then the mixture was poured into water and extracted with water. The organic layer was washed with a saturated aqueous solution of sodium chloride, dried over magnesium sulfate ($MgSO_4$) and concentrated to obtain a crude product. The crude product was purified by silica gel column chromatography (eluent: ether-hexane=1:10), giving 2 g of the title compond. The title compound will be referred to as "Compound 1."

The physicochemical properties of the resulting compound are shown in Table 1.

EXAMPLES 2–23

Following the general procedure of Example 1, the compounds shown in Table 1 as Compounds 2–11 were prepared.

Similarly, following the general procedure of Example 1, the free bases of the compounds listed in Table 1 as Compounds 12–23 were prepared and then converted to the hydrochlorides by treatment with 4N hydrogen chloride in ethyl acetate.

The physicochemical properties of these compounds (Compounds 2–23) are shown in Table 1 below.

EXAMPLE 24

Preparation of 2,6-di-tert-butyl-4-(3-carboxyphenylamino)phenol

A mixture of 6.6 g of 2,6-di-tert-butyl-1,4-benzoquinone, 4.2 g of m-aminobenzoic acid and 6 drops of acetic acid was stirred with heating at a temperature of 150°–160° C. for 2 hours and then allowed to cool. To the reaction mixture were added about 50 ml of water and then 200 ml of THF. Further a solution of 50 g of $Na_2S_2O_4$ in 300 ml of water was also added to the red mixture at room temperature, and the mixture was stirred for about 15 minutes until a decoloration took place. Then the mixture was poured into water and extracted with ethyl acetate. The organic layer was treated in the same manner as in Example 1 and the resulting crude product was purified by silica gel column chromatography (eluent: $CH_2Cl_2$-THF=5:1), giving 6.7 g of the title compound. The title compound will be referred to as "Compound 24."

The physicochemical properties of the resulting compound are shown in Table 1 below.

EXAMPLES 25–30

Following the general procedure of Example 24, the compounds shown in Table 1 as Compounds 25–29 were prepared.

Similarly, following the general procedure of Example 24, the free base of te compound listed in Table 1 as Compound 30 was prepared and then converted to the hydrochloride by treatment with 4N hydrogen chloride in ethyl acetate.

The physicochemical properties of these compounds (Compounds 25–30) are also shown in Table 1 below.

EXAMPLE 31

Preparation of 2,6-di-tert-butyl-4-(3-hydroxymethylphenylamino)phenol hydrochloride A 1.8 g quantity of the 4-(3-carboxyphenylamino)-2,6-di-tert-butylphenol prepared in Example 24 was dissolved in 30 ml of THF, and the solution was added dropwise at room temperature to a suspension of 1.7 g of $LiAlH_4$ in 150 ml of ethyl ether with stirring. Then the resulting mixture was refluxed for 3.5 hours. After cooling, water-containing ethyl ether and then water were carefully added to the reaction mixture to decompose the excess $LiAlH_4$. Subsequently the organic layer was separated, dried over $MgSO_4$ and concentrated to give a crude product. The crude product was dissolved in 100 ml of ethyl ether, and 6 ml of 4N hydrogen chloride in ethyl acetate was added to the solution. The crystals thus precipitated were filtered, washed with ethyl ether and air-dried, giving 1.5 g of the title compound (Compound 31).

The properties of Compound 31 are shown in Table 1 below.

EXAMPLES 32–40

Following the general procedure of Example 31, the compounds shown in Table 1 as Compounds 32–40 were prepared.

EXAMPLE 41

Preparation of 2,6-di-tert-butyl-4-[3-(1-hydroxyethyl)phenylamino]phenol hydrochloride A 1 g quantity of Compound 10, i.e., 4-(3-acetylphenylamino)-2,6-di-tert-butylphenol prepared in Example 10 was disoloved in 17 ml of ethanol and 3 ml of THF, and 200 mg of $NaBH_4$ was slowly added to the solution with ice cooling and stirring. The mixture was stirred for 1 hour. The reaction mixture was poured into water, and extracted with ethyl ether. The red organic layer was washed with a 10% aqueous solution of $Na_2S_2O_4$ until a decoloration took place, then washed with a saturated aqueous solution of sodium chloride, dried over $MgSO_4$ and concentrated to about 100 ml. A 6 ml quantity of a solution of 4N hydrogen chloride in ethyl acetate was added to the concentrate and the crystals thus precipitated were filtered, washed with ethyl ether and air-dried, giving 1 g of the title compound (Compound 41).

The properties of Compound 41 are shown in Table 1 below.

TABLE 1 t-Bu, HO, t-Bu substituted phenyl—NH—R¹

| Compound No. | R¹ | ¹H—NMR (δ, ppm, Internal Standard: TMS) | Melting point (°C.) |
|---|---|---|---|
| 1 | 4-F-phenyl | 6.80–7.10 (4H, m), 6.83 (2H, s), 5.37 (1H, brs), 4.91 (1H, s) 1.42 (18H, s) (CDCl₃) | 102–102.5 |

TABLE 1-continued

Structure: HO-(3,5-di-t-Bu-phenyl)-NH-R¹

| Compound No. | R¹ | ¹H—NMR (δ, ppm, Internal Standard: TMS) | Melting point (°C.) |
|---|---|---|---|
| 2 | 2-chlorophenyl | 6.60–7.35 (4H, m), 7.02 (2H, s), 5.95 (1H, brs), 5.04 (1H, s), 1.43 (18H, s) (CDCl₃) | 114–116 |
| 3 | 2-hydroxyphenyl | 6.80–7.18 (4H, m), 6.74 (2H, s), 5.50 (2H, brs), 4.82 (1H, s), 1.40 (18H, s) (CDCl₃) | 168–170 |
| 4 | 2-(trifluoromethyl)phenyl | 6.90–7.36 (4H, m), 6.99 (2H, s), 5.62 (1H, brs), 5.02 (1H, s), 1.43 (18H, s) (CDCl₃) | 81–81.5 |
| 5 | 4-(CH₂COOH)phenyl | 7.40 (2H, brs), 7.10 (2H, d, J = 8.6Hz), 6.96 (2H, s), 6.82 (2H, d, J = 8.6Hz), 5.00 (1H, brs), 3.54 (2H, s), 1.42 (18H, s) (CDCl₃) | >180 |
| 6 | 4-(CH₂COOC₂H₅)phenyl | 7.11 (2H, d, J = 8.6Hz), 6.96 (2H, s), 6.82 (2H, d, J = 8.6Hz), 5.50 (1H, brs), 4.94 (1H, s), 4.14 (2H, q, J = 7.0Hz), 3.51 (2H, s), 1.42 (18H, s), 1.24 (3H, t, J = 7.0Hz), (CDCl₃) | 119–120 |
| 7 | 4-OCH₃ phenyl | 6.84 (2H, s), 6.80–7.00 (4H, m), 5.30 (1H, brs), 4.83 (1H, s), 3.77 (3H, s), 1.41 (18H, s) (CDCl₃) | 94–94.5 |
| 8 | 3-(CH₂COOH)phenyl | 6.66–7.25 (4H, m), 6.97 (2H, s), 4.95 (1H, brs) 3.55 (2H, s), 1.42 (18H, s) (CDCl₃) | 132–133.5 |
| 9 | 4-(C(O)CH₃)phenyl | 7.83 (2H, d, J = 8.8Hz), 7.03 (2H, s), 6.80 (2H, d, J = 8.8Hz), 5.90 (1H, brs), 5.10 (1H, s), 2.50 (3H, s), 1.44 (18H, s) (CDCl₃) | 176–179 |
| 10 | 2-(C(O)CH₃)phenyl | 7.00–7.52 (4H, m), 7.00 (2H, s), 5.65 (1H, brs), 5.00 (1H, s), 2.55 (3H, s), 1.43 (18H, s) (CDCl₃) | 165–166 |

TABLE 1-continued

Structure: 3,5-di-t-Bu-4-hydroxyphenyl — with NH—R¹ at position (see diagram)

HO—[3,5-di-t-Bu-phenyl]—NH—R¹

| Compound No. | R¹ | ¹H—NMR (δ, ppm, Internal Standard: TMS) | Melting point (°C.) |
|---|---|---|---|
| 11 | —C₆H₄—CH(CH₃)COOH (para) | 7.14 (2H, d, J = 8.0Hz), 6.96 (2H, s), 6.92 (2H, d, J = 8.0Hz), 4.98 (1H, s), 3.64 (1H, q, J = 7.0Hz), 1.46 (3H, d, J = 7.0Hz), 1.42 (18H, s) (CDCl₃) | 178–181 |
| 12 | 2-(SCH₃)-phenyl (hydrochloride) | 7.11–7.91 (6H, m), 2.41 (3H, s), 1.36 (18H, s) (CDCl₃) | 124–127 (decomposition) |
| 13 | 3,4,5-tri-OCH₃-phenyl (hydrochloride) | 7.98 (3H, brs), 6.93 (2H, s), 6.28 (2H, s), 3.70 (6H, s), 3.57 (3H, s), 1.37 (18H, s) (DMSO—d₆) | >135 |
| 14 | 4-NH₂-phenyl (di-hydrochloride) | 7.51–7.21 (4H, m), 7.15 (2H, s), 1.41 (18H, s) (CD₃OD) | >225 |
| 15 | 4-(phenylthio)phenyl (hydrochloride) | 7.35 (2H, s), 7.41–7.11 (9H, m), 1.41 (18H, s) (CD₃OD) | 158–161 |
| 16 | 2-(phenylthio)phenyl (hydrochloride) | 7.45–6.65 (9H, m), 6.85 (2H, s), 1.35 (18H, s) (DMSO—d₆-CD₃OD) | 133–138 |
| 17 | 4-[S—(CH₂)₄—CH₃]-phenyl (hydrochloride) | 7.77 (2H, brs), 7.38 (1H, s), 7.18 (2H, d, J = 8.5 Hz), 6.91 (2H, s), 6.88 (2H, d, J = 8.5Hz), 2.76 (2H, t, J = 6.1Hz), 1.71–1.15 (6H, m), 1.37 (18H, s), 0.83 (3H, t, J = 6.5Hz) (DMSO—d₆) | 136.5–138.5 |

TABLE 1-continued

Structure: 3,5-di-t-Bu-4-HO-C₆H₂-NH-R¹

| Compound No. | R¹ | ¹H—NMR (δ, ppm, Internal Standard: TMS) | Melting point (°C.) |
|---|---|---|---|
| 18 | —C₆H₄—(CH₂)₃—CH₃ (hydrochloride) | 7.04–7.00 (6H, m), 2.50 (2H, brt, J = 7.0Hz), 1.37 (18H, s), 1.30–1.70 (4H, m), 0.89 (3H, brt, J = 6.5Hz) (DMSO—d₆) | 164–166 |
| 19 | 4-Cl-2-(—)-phenol with OH (hydrochloride) | 7.26 (2H, s), 7.21 (1H, dd, J = 8.5, 1.8Hz), 7.03 (1H, d, J = 1.8Hz), 6.97 (1H, d, J = 8.5Hz), 1.43 (18H, s) (CD₃OD) | 186–188 |
| 20 | —C₆H₄—CH₃ (hydrochloride) | 6.99, 6.96 (6H, brs), 2.21 (3H, s), 1.36 (18H, s), (DMSO—d₆) | 183–186 (decomposition) |
| 21 | —C₆H₄—(CH₂)₂—COOH (hydrochloride) | 7.45 (2H, d, J = 8.5Hz), 7.33 (2H, d, J = 8.5Hz), 7.23 (2H, s), 2.97 (2H, t, J = 7.1Hz), 2.63 (2H, t, J = 7.1Hz), 1.41 (18H, s) (CD₃OD) | 191–193 (decomposition) |
| 22 | —C₆H₄—(CH₂)₃—COOH (hydrochloride) | 6.98–6.91 (6H, m), 2.49 (2H, brt, J = 7.5Hz), 2.20 (2H, brt, J = 7.0Hz), 1.60–1.95 (2H, m), 1.36 (18H, s) (DMSO—d₆) | 187–189 (decomposition) |
| 23 | 4-HO-phenyl-CH₂COOH (hydrochloride) | 7.32 (2H, s), 7.30 (1H, d, J = 2.0Hz), 7.25 (1H, dd, J = 8.1, 2.0Hz), 7.01 (1H, d, J = 8.1Hz), 3.56 (2H, s), 1.41 (18H, s) (CD₃OD) | 228.5–229.5 (decomposition) |
| 24 | —C₆H₄—COOH (meta) | 7.98 (1H, brs), 7.57 (1H, brs), 7.00–7.30 (3H, m), 6.92 (2H, s), 6.65 (1H, brs) 1.38 (18H, s) (DMSO—d₆) | 257–258.5 (decomposition) |
| 25 | —C₆H₄—COOH (ortho) | 9.10 (1H, brs), 8.02 (1H, brd, J = 7.5Hz), 7.30 (1H, brt, J = 7.5Hz,), 7.07 (2H, s), 6.95 (1H, brd, J = 7.5Hz), 6.65 (1H, brt, J = 7.5Hz), 5.12 (1H, brs), 1.45 (18H, s) (CDCl₃) | 215–225 (decomposition) |

TABLE 1-continued

Structure: 3,5-di-t-Bu-4-HO-C6H2-NH-R¹ (2,6-di-t-butyl-4-amino-phenol derivative with HO at position shown)

| Compound No. | R¹ | ¹H—NMR (δ, ppm, Internal Standard: TMS) | Melting point (°C.) |
|---|---|---|---|
| 26 | –C₆H₄–COOH (para) | 8.34 (1H, brs), 7.71 (2H, d, J = 8.8Hz), 6.95 (2H, s), 6.86 (2H, d, J = 8.8Hz), 6.75 (1H, brs), 1.39 (18H, s) (DMSO—d₆) | 242–244 (decomposition) |
| 27 | –C₆H₃(Cl)(COOH) | 7.95 (1H, d, J = 2.4Hz), 7.22 (1H, dd, J = 9.2 2.4Hz), 7.03 (2H, s), 6.88 (1H, d, J = 9.2Hz), 5.18 (1H, s), 1.44 (18H, s), (CDCl₃) | >225 |
| 28 | –C₆H₄–CN (para) | 7.41 (2H, d, J = 8.8Hz), 7.00 (2H, s), 6.76 (2H, d, J = 8.8Hz), 5.88 (1H, s), 5.13 (1H, s), 1.43 (18H, s), (CDCl₃) | 176.5–178.5 |
| 29 | –C₆H₃(CH₃)(COOH) | 7.80 (1H, d, J = 2.2Hz), 7.12 (1H, dd, J = 9.2, 2.2Hz), 7.03 (2H, s), 6.90 (1H, d, J = 9.2Hz), 5.07 (1H, brs), 2.25 (3H, s), 1.45 (18H, s) (CDCl₃) | 217.5–218.5 (decomposition) |
| 30 | –C₆H₃(OH)(COOH) (hydrochloride) | 7.56 (1H, d, J = 2.3Hz), 7.22 (1H, dd, J = 2.3Hz), 6.91 (2H, s), 6.85 (1H, d, J = 9.3Hz), 1.37 (18H, s) (DMSO—d₆) | 220–221 (decomposition) |
| 31 | –C₆H₄–CH₂OH (meta) (hydrochloride) | 6.70–7.20 (4H, m), 6.94 (2H, s), 4.39 (2H, s), 1.37 (18H, s) (DMSO—d₆) | 218–219 (decomposition) |
| 32 | –C₆H₄–CH₂OH (ortho) (hydrochloride) | 7.30–6.80 (4H, m), 6.86 (2H, s), 4.50 (2H, s), 1.36 (18H, s) (DMSO—d₆) | >135 (decomposition) |
| 33 | –C₆H₄–(CH₂)₂–OH (hydrochloride) | 7.04–6.98 (6H, m), 3.55 (2H, t, J = 7.2Hz), 2.63 (2H, t, J = 7.2Hz), 1.37 (18H, s) (DMSO—d₆) | 205–207 (decomposition) |

TABLE 1-continued

Structure: 3,5-di-t-Bu-4-hydroxyphenyl-NH-R¹ (HO on ring with two t-Bu groups ortho, NH-R¹ para)

| Compound No. | R¹ | ¹H—NMR (δ, ppm, Internal Standard: TMS) | Melting point (°C.) |
|---|---|---|---|
| 34 | –C₆H₄–(CH₂)₃—OH (hydrochloride) | 7.38 (4H, s), 7.26 (2H, s), 3.57 (2H, t, J = 6.3Hz), 2.77 (2H, t, J = 8.3Hz), 1.70–2.01 (2H, m), 1.41 (18H, s) (CD₃OD) | 193–196 (decomposition) |
| 35 | –C₆H₄–(CH₂)₄—OH (hydrochloride) | 6.96–6.90 (6H, m), 3.39 (2H, brt, J = 7.1Hz), 2.47 (2H, brt, J = 7.1Hz), 1.25–1.70 (4H, m), 1.36 (18H, s) (DMSO—d₆) | 170–171 (decomposition) |
| 36 | –C₆H₄–(CH₂)₂—OH (hydrochloride) | 6.54–7.16 (4H, m), 6.92 (2H, s), 3.57 (2H, t, J = 7.0Hz), 2.62 (2H, t, J = 7.0Hz), 1.37 (18H, s) (DMSO—d₆) | 176–179 (decomposition) |
| 37 | –C₆H₄–CH(CH₃)CH₂OH (hydrochloride) | 7.05 (2H, d, J = 8.0Hz), 6.88 (2H, d, J = 8.0Hz), 6.93 (2H, s), 2.23–3.57 (2H, m), 2.50–2.80 (1H, m), 1.36 (18H, s), 1.14 (3H, d, J = 7.0Hz) (DMSO—d₆) | 187–188 (decomposition) |
| 38 | –C₆H₃(Cl)(CH₂OH) (hydrochloride) | 6.83–7.27 (3H, m), 6.83 (2H, s), 4.48 (2H, s), 1.36 (18H, s) (DMSO—d₆) | 98–105 |
| 39 | –C₆H₃(OH)–(CH₂)₂—OH (hydrochloride) | 7.31 (2H, s), 7.18–7.25 (2H, m), 6.96 (1H, d, J = 8.8Hz), 3.70 (2H, d, J = 6.6Hz), 2.75 (2H, d, J = 6.6Hz), 1.41 (18H, s) (CD₃OD) | >145 (decomposition) |
| 40 | –C₆H₃(CH₃)(CH₂OH) (hydrochloride) | 6.69–7.17 (3H, m), 6.80 (2H, s), 4.45 (2H, s), 2.22 (3H, s), 1.36 (18H, s) (DMSO—d₆) | >133 (decomposition) |

TABLE 1-continued $$\text{HO}-\underset{\underset{t\text{-Bu}}{|}}{\overset{\overset{t\text{-Bu}}{|}}{\bigcirc}}-\text{NH}-\text{R}^1$$

| Compound No. | R$^1$ | $^1$H—NMR (δ, ppm, Internal Standard: TMS) | Melting point (°C.) |
| --- | --- | --- | --- |
| 41 | ![structure with CHCH$_3$-OH group on benzene ring] (hydrochloride) | 6.63–7.17 (4H, m), 6.92 (2H, s), 4.60 (2H, q, J = 6.5Hz), 1.37 (18H, s), 1.28 (3H, d, J = 6.5Hz) (DMSO—d$_6$) | 167–168 (decomposition) |

EXAMPLE 42

Preparation of 4-(4-dimethylaminophenylamino)-2,6-di-tert-butylphenol dihydrochloride (Compound 42)

A 2.6 g quantity of 2,6-di-tert-butyl-1,4-benzoquinone and 2.6 g of 4-dimethylaminoaniline were dissolved in 60 ml of THF, and 0.3 ml of (C$_2$H$_5$)$_2$O.BF$_3$ was added to the solution. The resulting mixture was refluxed with heating for 7 hours. The reaction mixture was concentrated to give a crude product which was purified by silica gel column chromatography (eluent: diethyl ether-hexane=1:5), giving red-purple crystals.

The crystals were dissolved in 150 ml of THF. To the solution was added 150 ml of an aqueous solution of 21 g of Na$_2$S$_2$O$_4$ at room temperature, and the mixture was stirred for 10 minutes. Then water was added thereto and the mixture was extracted with diethyl ether. The organic layer was dried over MgSO$_4$ and concentrated. The resulting oil was dissolved in a small amount of diethyl ether. To this solution was added 3 ml of a solution of 4N hydrogen chloride in ethyl acetate, and the crystals thus precipitated were filtered. The crystals were recrystallized from ethanol-diethyl ether, giving 1.8 g of the title compound.

The properties (melting point and $^1$H-NMR data) of the resulting compound are shown in Table 3 below.

EXAMPLES 43–51

Preparation of Compounds 43–51

Following the general procedure of Example 42, the contemplated compounds (Compounds 43–51) listed in Table 2 were prepared.

Table 3 below shows the properties of the resulting compounds.

EXAMPLE 52

Preparation of ethyl 3-(4-hydroxy-2,3,5-trimethylphenylamino)cinnamate hydrochloride (Compound 52)

To a solution of 2.2 ml of pyridine in 60 ml of dichloroethane was added 0.73 ml of TiCl$_4$, and the mixture was stirred with heating at 90° C. for 20 minutes. To the mixture were added 2 g of 2,3,6-trimethyl-1,4-benzoquinone and 3 g of ethyl 3-aminocinnamate hydrochloride, and the mixture was heated at 90° C. for 30 minutes. Then the mixture was concentrated by evaporating the solvent under reduced pressure, and the oily reaction mixture was purified by silica gel column chromatography (eluent: diethyl ether-hexane=1:9→1:4), giving 1 g of a red-yellow oil.

The product was dissolved in 150 ml of THF, and to this solution was added an aqueous solution of 10 g of Na$_2$S$_2$O$_4$ in 150 ml of water and the mixture was stirred for 10 minutes. Then, water was added to the mixture and the mixture was subjected to extraction with ethyl acetate. The organic layer was washed with water, dried over MgSO$_4$ and concentrated, giving an oil. The resulting oil was dissolved in diethyl ether, and to this solution was added 1 ml of 4N hydrogen chloride ethyl acetate. The salt thus precipitated was filtered and recrystallized from ethanoldiethyl ether, giving 0.75 g of the title compound.

Table 3 below shows the properties of the resulting compound.

EXAMPLE 53

Preparation of 4-(4-benzoylaminophenylamino)-2,6-di-tert-butylphenol hydrochloride (Compound 53)

A 1.6 g quantity of 2,6-di-tert-butyl-1,4-benzoquinone, 1.3 g of p-phenylenediamine dihydrochloride, 1.2 g of sodium acetate and 0.23 ml of (C$_2$H$_5$)$_2$O.BF$_3$ were suspended in 50 ml of THF. The resulting suspension was refluxed with heating for 15 hours. After cooling, a solution of 20 g of Na$_2$S$_2$O$_4$ in 150 ml of water was added to the reaction mixture, and the mixture was stirred at room temperature for 30 minutes and then extracted with ethyl acetate. The organic layer was dried over MgSO$_4$ and concentrated to give a major product which was purified by silica gel column chromatography (eluent: diethyl ether-hexane=1:1), giving 1.5 g of an oil. To the solution were added with ice-cooling 538 mg of triethylamine and then 748 mg of benzoyl chloride, and the mixture was stirred at room temperature for 1.5 hours. Then water was added thereto and the mixture was extracted with chloroform. The organic layer was dried over MgSO$_4$ and concentrated. The resulting concentrate was purified by silica gel column chromatography (eluent: diethyl ether-hexane=1:1) to give an oil. The oil was dissolved in a small amount of diethyl ether. To this solution was added 3 ml of a solution of 4N hydrogen chloride in ethyl acetate, and the crystals thus precipitated were filtered. The crystals were recrystallized from ethanol-diethyl ether, giving 1.7 g of the title compound.

Table 3 below shows the properties of the resulting compound.

EXAMPLES 54–57

Preparation of Compounds 54–57

Following the general procedure of Example 53, the contemplated compounds (Compounds 54–57) listed in Table 2 were prepared.

Table 3 below shows the properties of the resulting compounds.

EXAMPLE 58

Preparation of 2,6-di-tert-butyl-4-(2-phenylsulfonylaminophenylamino)phenol hydrochloride (Compound 58)

A 1 g quantity of 2,6-di-tert-butyl-1,4-benzoquinone and 0.8 g of o-phenylenediamine were dissolved in 50 ml of THF. To this solution was added 0.15 ml of $(C_2H_5)_2O.BF_3$ and the resulting mixture was refluxed with heating for 15 hours. After cooling, a solution of 20 g of $Na_2S_2O_4$ in 250 ml of water was added to the reaction mixture, and the mixture was stirred at room temperature for 30 minutes and then extracted with ethyl acetate. The organic layer was dried over $MgSO_4$ and concentrated to give a crude product which was purified by silica gel column chromatography (eluent: diethyl ether-hexane=1:5), giving 1 g of an oil.

The oil was dissolved in 10 ml of DMA. To the solution were added with ice-cooling 1.28 g of pyridine and then 570 mg of benzenesulfonyl chloride, and the mixture was stirred at room temperature for 1.5 hours. Then water was added thereto and the mixture was extracted with chloroform. The organic layer was dried over $MgSO_4$ and concentrated. The resulting concentrate was purified by silica gel column chromatography (eluent: chloroform-hexane=1:1) to give an oil. The oil was dissolved in a small amount of diethyl ether. To this solution was added 3 ml of a solution of 4N hydrogen chloride in ethyl acetate, and the crystals thus precipitated were filtered. The crystals were recrystallized from ethanol-diethyl ether, giving 1 g of the title compound.

Table 3 below shows the properties of the resulting compound.

EXAMPLE 59

Preparation of Compound 59

Following the general procedure of Example 58, the contemplated compound (Compound 59) listed in Table 2 was prepared.

Table 3 shows the properties of the resulting compound.

EXAMPLE 60

Preparation of 2,6-di-tert-butyl-4-(2-ethoxycarbonylphenylamino)-phenol hydrochloride (Compound 60)

A mixture of 10 g quantity of 2,6-di-tert-butyl-1,4-benzoquinone, 6.3 g of anthranylic acid and 0.2 ml of acetic acid was heated at 150° to 160° C. for 1 hour. The resulting reaction mixture was cooled and dissolved in 200 ml of THF. To the solution was added a solution of 50 g of $Na_2S_2O_4$ in 500 ml of water, and the mixture was stirred at room temperature for 30 minutes and then extracted with ethyl acetate. The organic layer was dried over $MgSO_4$ and concentrated to precipitate crystals which were purified by silica gel column chromatography (eluent: dichloromethane-diethyl ether=8:1), giving 5.5 g of 2,6-di-tert-butyl-4-(2-carboxyphenylamino)phenol (Compound 25).

Melting point: 215°–225° C. (decomposition).

A 1 g portion of the compound thus obtained was dissolved in 5 ml of DMF. To the solution were added 500 mg of potassium carbonate and 350 mg of ethyl bromide, and the mixture was stirred at room temperature for 20 hours. Then the mixture was poured into a 10% aqueous solution of $Na_2S_2O_4$ and extracted with ethyl acetate. The organic layer was washed with water, dried over $MgSO_4$ and concentrated. The resulting oily substance was purified by silica gel column chromatography (eluent: diethyl ether-hexane=1:5), and then dissolved in a small amount of diethyl ether. To this solution was added 2 ml of a solution of 4N hydrogen chloride in ethyl acetate, and the crystals thus precipitated were filtered, giving 0.75 g of the title compound as pale yellow crystals.

Table 3 below shows the properties of the resulting compound.

EXAMPLE 61

Preparation of 4-(2-benzylaminocarbonylphenylamino)-2,6-di-tert-butylphenol (Compound 61)

A 1 g quantity of 2,6-di-tert-butyl-4-(2-carboxyphenylamino)phenol (Compound 25) was dissolved in 20 ml of DMF. To the solution were added with ice-cooling 340 mg of benzylamine and 570 mg of DEPC and then added a solution of 330 mg of triethylamine in 5 ml of DMF over 20 minutes. Then the reaction mixture was stirred at room temperature for 20 hours, and then poured into water, and extracted with ethyl acetate. The organic layer was washed with water, dried over $MgSO_4$ and concentrated to give a crude product which was purified by silica gel column chromatography (eluent: diethyl ether-hexane=1:10→1:5), giving 1.1 g of the title compound as white crystals.

Table 3 shows the properties of the resulting compound.

EXAMPLES 62–75

Following the general procedure of Example 61, the compounds listed in Table 2 as Compounds 62–75 were prepared.

Table 3 below shows the properties of the resulting compounds.

EXAMPLE 76

Preparation of 2,6-di-tert-butyl-4-(4-hydrazinocarbonylmethylphenylamino)phenol (Compound 76)

A mixture of 6 g of 2,6-di-tert-butyl-1,4-benzoquinone, 15 g of ethyl 4-aminophenylacetate, 120 ml of THF and 0.5 ml of $(C_2H_5)_2O.BF_3$ was refluxed with heating for 16 hours. The resulting reaction mixture was cooled. To the reaction mixture was added a solution of 50 g of $Na_2S_2O_4$ in 250 ml of water, and the mixture was stirred at room temperature for 30 minutes and then poured into water and extracted with ethyl acetate. The organic layer was washed with water, drived over MgSO$_4$ and concentrated to give a crude product which was purified by silica gel column chromatography (eluent: diethyl ether-hexane=1:4), giveing 10 g of 2,6-di-ter-butyl-4-(4-ethoxycarbonylmethylphenylamino)phenol (Compound 6). Melting point:119°-120° C.

A 2.4 g portion of the compound thus obtained was dissolved in 25 ml of hydrazine hydrate and 25 ml of ethanol, and the solution was heated at 100° C. for 40 minutes. Then the reaction mixture was poured into water and extracted with ethyl acetate. The organic layer was washed with a 10% aqueous solution of Na$_2$S$_2$O$_4$ and then with water, dried over MgSO$_4$ and concentrated. The crystals thus precipitated were recrystallized from a mixture of diethyl ether-hexane (1:4), giving 1.8 g of the title compound as white crystals.

Table 3 below shows the properties of the resulting compound.

EXAMPLE 77

Preparation of 4-(4-benzylaminophenylamino)-2,6-di-tert-butylphenol dihydrochloride (Compound 77)

To a suspension of 466 mg of LiAlH$_4$ in 30 ml of THF was added a solution of 1.7 g of 4-(4-benzoylaminophenylamino)-2,6-di-tert-butylphenol (free base of Compound 53) in 30 ml of THF, and the mixture was refluxed for 5.5 hours. After cooling, a solution of 15 g of Na$_2$S$_2$O$_4$ in 60 ml of water was added to the reaction mixture, and the resulting mixture was stirred at room temperature for 10 minutes. Then water was added thereto and the mixture was extracted with diethyl ether. The organic layer was dried over MgSO$_4$ and concentrated. The oil thus obtained was dissolved in a small amount of diethyl ether. To this solution was added 2 ml of a solution of 4N hydrogen chloride in ethyl acetate, and the crystals thus precipitated were filtered and recrystallized from isopropanol-diethyl ether, giving 450 mg of the title compound as white crystals.

Table 3 below shows the properties of the resulting compound.

EXAMPLE 78

Following the general procedure of Example 77, the compound listed in Table 2 as Compound 78 was prepared.

Table 3 below shows the properties of the resulting compound.

TABLE 2

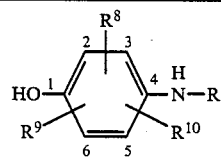

| Compound No. | R$^8$ | R$^9$ | R$^{10}$ | R |
|---|---|---|---|---|
| 42 | 2-t-Bu | 6-t-Bu | H | —⟨phenyl⟩—N(CH$_3$)$_2$ (di-hydrochloride) |
| 43 | 2-t-Bu | 6-t-Bu | H | —⟨phenyl⟩—NHCH$_3$ (di-hydrochloride) |
| 44 | 2-t-Bu | 6-t-Bu | H | —⟨phenyl⟩—NH—⟨phenyl⟩ (di-hydrochoride) |
| 45 | 2-t-Bu | 6-t-Bu | H | —⟨phenyl⟩—CH=CH—C(=O)OCH$_2$CH$_3$ (meta) |
| 46 | 2-t-Bu | 6-t-Bu | H | —⟨phenyl⟩—CH=CH—C(=O)OCH$_2$CH$_3$ (para) (hydrochoride) |

TABLE 2-continued

Structure: HO-benzene ring with positions labeled 1,2,3,4,5,6; R⁸ at position 2/3, R⁹ at position 6, R¹⁰ at position 5, and NHR at position 4.

| Compound No. | R⁸ | R⁹ | R¹⁰ | R |
|---|---|---|---|---|
| 47 | 2-t-Bu | 6-t-Bu | H | 4-(CH=CH-COOH)-phenyl (hydrochloride) |
| 48 | 2-t-Bu | 6-t-Bu | H | 2-(CH=CH-COOH)-phenyl |
| 49 | 2-t-Bu | 6-t-Bu | H | 3-(CH=CH-COOH)-phenyl |
| 50 | 2-t-Bu | 6-t-Bu | H | 4-(CH=CH-CO-(CH₂)₄-CH₃)-phenyl |
| 51 | 2-t-Bu | 6-t-Bu | H | 3-(CH=CH-CO-(CH₂)₄-CH₃)-phenyl |
| 52 | 2-CH₃ | 3-CH₃ | 6-CH₃ | 3-(CH=CH-COOCH₂CH₃)-phenyl (hydrochloride) |
| 53 | 2-t-Bu | 6-t-Bu | H | 4-(NHC(O)-C₆H₅)-phenyl (hydrochloride) |
| 54 | 2-t-Bu | 6-t-Bu | H | 4-(NHC(O)CH₃)-phenyl (hydrochloride) |

TABLE 2-continued
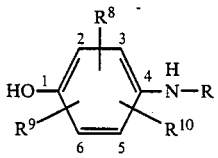
| Compound No. | $R^8$ | $R^9$ | $R^{10}$ | R |
|---|---|---|---|---|
| 55 | 2-t-Bu | 6-t-Bu | H | 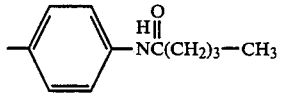 (hydrochloride) |
| 56 | 2-t-Bu | 6-t-Bu | H | 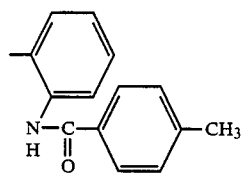 |
| 57 | 2-t-Bu | 6-t-Bu | H | 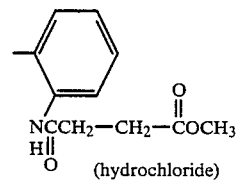 (hydrochloride) |
| 58 | 2-t-Bu | 6-t-Bu | H | 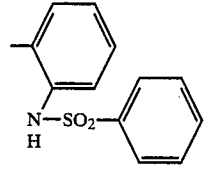 (hydrochloride) |
| 59 | 2-t-Bu | 6-t-Bu | H | 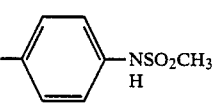 |
| 60 | 2-t-Bu | 6-t-Bu | H | 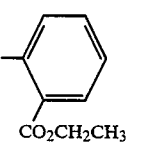 (hydrochloride) |
| 61 | 2-t-Bu | 6-t-Bu | H | 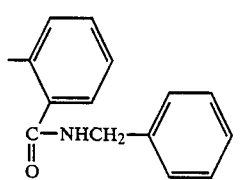 |

TABLE 2-continued

Structure: HO-1, R⁸ at 2, position 3, R⁹ at position 5(bottom), position 6, NH-R at 4, R¹⁰ at 5.

| Compound No. | R⁸ | R⁹ | R¹⁰ | R |
|---|---|---|---|---|
| 62 | 2-t-Bu | 6-t-Bu | H | 2-methylphenyl-C(=O)-N(piperidine) |
| 63 | 2-t-Bu | 6-t-Bu | H | 4-methylphenyl-C(=O)-NH-(CH$_2$)$_8$-CH$_3$ (hydrochloride) |
| 64 | 2-t-Bu | 6-t-Bu | H | 4-methylphenyl-C(=O)-NH-cyclohexyl (hydrochloride) |
| 65 | 2-t-Bu | 6-t-Bu | H | 2-methylphenyl-C(=O)-NH-cyclohexyl |
| 66 | 2-t-Bu | 6-t-Bu | H | 3-methylphenyl-CH=CH-C(=O)-NH-(CH$_2$)$_5$-CH$_3$ (hydrochloride) |
| 67 | 2-t-Bu | 6-t-Bu | H | 4-methylphenyl-CH=CH-C(=O)-NH-cyclohexyl (hydrochloride) |
| 68 | 2-t-Bu | 6-t-Bu | H | 4-methylphenyl-CH$_2$-CH$_2$-C(=O)-N(piperidine) (hydrochloride) |
| 69 | 2-t-Bu | 6-t-Bu | H | 4-methylphenyl-CH$_2$-CH$_2$-C(=O)-N(morpholine) (hydrochloride) |

TABLE 2-continued

Structure: HO-(1)-phenyl ring with R⁸ at 2, (3), NH-R at 4, R⁹ at 5(?), R¹⁰ at position; positions 2,3,4,5,6 labeled; R⁹ and R¹⁰ on ring.

| Compound No. | R⁸ | R⁹ | R¹⁰ | R |
|---|---|---|---|---|
| 70 | 2-t-Bu | 6-t-Bu | H | -C₆H₄-CH₂CH₂-C(O)-NH-cyclohexyl (hydrochloride) |
| 71 | 2-t-Bu | 6-t-Bu | H | -C₆H₄-CH₂-C(O)-N(morpholine) (hydrochloride) |
| 72 | 2-t-Bu | 6-t-Bu | H | -C₆H₄-CH₂-C(O)-NH-(CH₂)₂-CH₃ (hydrochloride) |
| 73 | 2-t-Bu | 6-t-Bu | H | -C₆H₄-CH₂-C(O)-N(piperidine) (hydrochloride) |
| 74 | 2-t-Bu | 6-t-Bu | H | -C₆H₄-CH₂-C(O)-NH-cyclohexyl (hydrochloride) |
| 75 | 2-t-Bu | 6-t-Bu | H | -C₆H₄-CH₂-C(O)-NH-CH₂-C₆H₅ (hydrochloride) |
| 76 | 2-t-Bu | 6-t-Bu | H | -C₆H₄-C(O)-NHNH₂ |
| 77 | 2-t-Bu | 6-t-Bu | H | -C₆H₄-NH-CH₂-C₆H₅ (di-hydrochloride) |

TABLE 2-continued

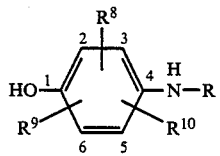

| Compound No. | $R^8$ | $R^9$ | $R^{10}$ | R |
|---|---|---|---|---|
| 78 | 2-t-Bu | 6-t-Bu | H | ![structure: 4-(N(H)-(CH$_2$)$_4$-CH$_3$)phenyl-] (di-hydrochloride) |

TABLE 3

| Compound No. | $^1$H—NMR ($\delta$, ppm, Internal Standard: TMS) | Melting point (°C.) |
|---|---|---|
| 42 | 6.85–7.45 (6H, m), 2.87 (6H, s), 1.56 (18H, s) (Py-d$_5$) | >155 (decomposition) |
| 43 | 7.47 (2H, d, J = 9.2Hz), 7.23 (2H, d, J = 9.2Hz), 7.11 (2H, s), 3.03 (3H, s), 1.41 (18H, s) (CD$_3$OD) | 230–232 (decomposition) |
| 44 | 7.15–7.45 (9H, m), 7.25 (2H, s), 1.57 (18H, s) (Py-d$_5$) | >170 (decomposition) |
| 45 | 7.60 (1H, d, J = 16.0Hz), 6.80–7.30 (4H, m), 6.99 (2H, s), 6.34 (1H, d, J = 16.0Hz), 5.50 (1H, brs), 5.00 (1H, s), 4.25 (2H, q, J = 7.0Hz), 1.43 (18H, s), 1.32 (3H, t, J = 7.0Hz) (CDCl$_3$) | 156–157.5 |
| 46 | 7.60 (1H, d, J = 15.8Hz), 7.30–7.51 (4H, m), 7.23 (2H, s), 6.31 (1H, d, J = 15.8Hz), 4.25 (2H, q, J = 7.3Hz), 1.41 (18H, s), 1.33 (3H, t, J = 7.3Hz) (CDCl$_3$—CD$_3$OD) | >55 (decomposition) |
| 47 | 7.63 (1H, d, J = 16.1Hz), 7.56 (2H, d, J = 8.3Hz), 7.17 (2H, d, J = 8.3Hz), 7.13 (2H, s), 6.35 (1H, d, J = 16.1Hz), 1.43 (18H, s) (CD$_3$OD) | >165 (decomposition) |
| 48 | 8.05 (1H, d, J = 15.8Hz), 6.75–7.56 (4H, m), 6.94 (2H, s), 6.41 (1H, d, J = 15.8Hz), 4.99 (2H, brs), 1.42 (18H, s) (CDCl$_3$) | 228–229 (decomposition) |
| 49 | 7.70 (1H, d, J = 16.0Hz), 6.84–7.30 (4H, m), 6.99 (2H, s), 6.36 (1H, d, J = 16.0Hz), 5.00 (1H, s), 1.44 (18H, s) (CDCl$_3$) | 185–186 |
| 50 | 7.49 (1H, d, J = 16.0Hz), 7.40 (2H, d, J = 8.5Hz), 6.82 (2H, d, J = 8.5Hz), 6.56 (1H, d, J = 16.0Hz), 5.82 (1H, brs), 5.06 (1H, s), 2.62 (2H, t, J = 7.2Hz), 1.20–1.80 (6H, m), 1.43 (18H, s), 0.90 (3H, brt, J = 6.1Hz) (CDCl$_3$) | 173–174 |
| 51 | 7.47 (1H, d, J = 16.1Hz), 6.80–7.30 (4H, m), 6.99 (2H, s), 6.64 (1H, d, J = 16.1Hz), 5.50 (1H, brs), 5.00 (1H, s), 2.63 (2H, t, J = 7.0Hz), 1.20–1.90 (6H, m), 1.43 (18H, s), 0.90 (3H, brt, J = 5.7Hz) (CDCl$_3$) | 128–129 |
| 52 | 7.47 (1H, d, J = 16.0Hz), 6.50–7.20 (5H, m), 6.32 (1H, d, J = 16.0Hz), 4.16 (2H, q, J = 7.0Hz), 2.13 (6H, s), 2.00 (3H, s), 1.24 (3H, t, J = 7.0Hz) (DMSO-d$_6$) | 161–163 |
| 53 | 7.18–8.13 (4H, m) 7.18–7.61 (7H, m), 1.43 (18H, s) (CD$_3$OD) | 222.5–224.5 (decomposition) |
| 54 | 7.77 (2H, d, J = 8.8Hz), 7.38 (2H, d, J = 8.8Hz), 7.23 (2H, brs), 2.15 (3H, s), 1.41 (18H, s) (CD$_3$OD) | 233–234.5 (decomposition) |
| 55 | 7.78 (2H, d, J = 8.8Hz), 7.36 (2H, d, J = 8.8Hz), 7.23 (2H, brs), 2.38 (2H, t, J = 7.1Hz), 1.21–1.81 (4H, m), 1.41 (18H, s), 0.95 (3H, t, J = 6.8Hz) (CD$_3$OD) | 211–213 (decomposition) |
| 56 | 7.98–8.18 (2H, m), 7.47 (2H, d, J = 8.5Hz), 7.15 (2H, d, J = 8.5Hz), 7.01–7.21 (2H, m), 6.73 (2H, s), 5.46 (1H, brs), 4.83 (1H, s), 2.36 (3H, s), 1.36 (18H, s) (CDCl$_3$) | 165–166.5 (decomposition) |
| 57 | 7.55–7.97 (3H, m) 7.41 (2H, s), 7.35–7.41 (1H, m), 3.66 (3H, s), 3.31 (2H, t, J = 5.7Hz), 2.95 (2H, t, J = 5.7Hz), 1.48 (18H, s) (CD$_3$OD) | 238.5–240.5 (decomposition) |
| 58 | 7.35–7.88 (6H, m), 6.93–7.10 (2H, m), 6.76 (2H, s), 6.50–6.71 (1H, m), 1.41 (18H, s) (CDCl$_3$—CD$_3$OD) | 152.5–154.5 (decomposition) |
| 59 | 7.38 (4H, brs), 7.23 (2H, s), 3.00 (3H, s), 1.43 (18H, s) (CD$_3$OD) | 205–207 (decomposition) |
| 60 | 7.95 (1H, dd, J = 7.9, 1.5Hz), 7.05 (2H, s), 6.93–7.38 (2H, m), 6.54–6.73 (1H, m), 5.07 (1H, s), 4.35 (2H, q, J = 7.0Hz), 1.43 (18H, s), 1.40 (3H, t, J = 7.0Hz) (CDCl$_3$) | 90.5–91.5 (decomposition) |
| 61 | 9.22 (1H, s), | 186–187 |

TABLE 3-continued

| Compound No. | ¹H—NMR (δ, ppm, Internal Standard: TMS) | Melting point (°C.) |
|---|---|---|
|  | 7.13–7.45 (8H, m),<br>7.05 (2H, s),<br>6.53–6.71 (1H, m),<br>6.42 (1H, brs), 5.00 (1H, s),<br>4.64 (1H, s), 4.58 (1H, s),<br>1.43 (18H, s) (CDCl₃) | (decomposition) |
| 62 | 7.17–6.64 (4H, m),<br>6.98 (2H, s), 4.94 (1H, s),<br>3.48–3.70 (4H, m),<br>1.50–1.75 (6H, m),<br>1.42 (18H, s) (CDCl₃) | 200–202 |
| 63 | 7.65 (2H, d, J = 8.5Hz),<br>6.92 (2H, s),<br>6.88 (2H, d, J = 8.5Hz),<br>3.18 (2H, m), 1.38 (18H, s),<br>1.10–1.70 (14H, m),<br>0.86 (3H, brt, J = 6.0Hz)<br>(DMSO-d₆) | 153–155 |
| 64 | 7.68 (2H, d, J = 8.5Hz),<br>6.94 (2H, s),<br>6.88 (2H, d, J = 8.5Hz),<br>3.70 (1H, m),<br>1.02–1.98 (10H, m),<br>1.38 (18H, s) (CDCl₃) | 187–190<br>(decomposition) |
| 65 | 9.15 (1H, s),<br>7.15–7.42 (3H, m),<br>7.07 (2H, s),<br>6.54–6.73 (1H, m),<br>5.98 (1H, brs), 4.97 (1H, s),<br>3.95 (1H, m),<br>1.30–2.20 (10H, m),<br>1.42 (18H, s) (CDCl₃) | 239–240 |
| 66 | 8.09 (1H, brs),<br>7.27 (1H, d, J = 16.2Hz),<br>6.80–7.30 (4H, m),<br>6.92 (2H, s),<br>6.50 (1H, d, J = 16.2Hz),<br>3.18 (2H, m),<br>1.10–1.60 (8H, m),<br>1.37 (18H, s),<br>0.87 (3H, brt, J = 5.7Hz)<br>(DMSO-d₆) | 184–185<br>(decomposition) |
| 67 | 8.05 (1H, d, J = 15.5Hz),<br>7.55 (2H, d, J = 8.1Hz),<br>7.28 (2H, s),<br>7.27 (2H, d, J = 8.1Hz),<br>6.93 (1H, d, J = 15.5Hz),<br>3.97–4.21 (1H, m),<br>1.83–2.21 (2H, m),<br>1.56 (18H, s),<br>1.01–1.65 (8H, m)<br>(Py-d₅-D₂O) | >170<br>(decomposition) |
| 68 | 7.45 (2H, d, J = 8.8Hz),<br>7.33 (2H, d, J = 8.8Hz),<br>7.23 (2H, s),<br>3.31–3.60 (4H, m),<br>2.61–3.05 (4H, m),<br>1.41 (18H, s),<br>1.15–1.70 (6H, m)<br>(CD₃OD) | 192.5–193.5<br>(decomposition) |
| 69 | 7.45 (2H, d, J = 8.7Hz),<br>7.33 (2H, d, J = 8.7Hz),<br>7.23 (2H, s), 3.55 (2H, s),<br>3.46 (2H, s),<br>2.60–3.05 (4H, m),<br>1.41 (18H, s) (CD₃OD) | 170–171<br>(decomposition) |
| 70 | 7.39 (4H, s), 7.25 (2H, s),<br>3.65–3.41 (1H, m),<br>2.97 (2H, t, J = 7.0Hz),<br>2.51 (2H, t, J = 7.0Hz),<br>1.83–1.10 (10H, m),<br>1.41 (18H, s) (CD₃OD) | >141<br>(decomposition) |
| 71 | 7.43 (4H, s), 7.26 (2H, s)<br>3.85 (2H, s), 3.58 (4H, s),<br>1.41 (18H, s) (CD₃OD) | 196–198<br>(decomposition) |
| 72 | 7.48 (2H, d, J = 8.8Hz),<br>7.33 (2H, d, J = 8.8Hz),<br>7.21 (2H, s), 3.55 (2H, s),<br>3.13 (2H, t, J = 6.5Hz),<br>1.41–1.71 (2H, m),<br>1.41 (18H, s),<br>0.88 (3H, t, J = 6.7Hz)<br>(CD₃OD) | 225–226<br>(decomposition) |
| 73 | 7.43 (4H, s), 7.23 (2H, s),<br>3.85 (2H, s),<br>3.43–3.70 (4H, m),<br>1.41–1.78 (6H, m),<br>1.41 (18H, s) (CD₃OD) | 95–98<br>(decomposition) |
| 74 | 7.48 (2H, d, J = 8.7Hz),<br>7.35 (2H, d, J = 8.7Hz),<br>7.23 (2H, s), 3.55 (2H, s),<br>3.41–3.51 (1H, m),<br>1.41–2.01 (6H, m),<br>1.41 (18H, s) (CD₃OD) | 228–231<br>(decomposition) |
| 75 | 7.48 (2H, d, J = 8.8Hz),<br>7.33 (2H, d, J = 8.8Hz),<br>7.23 (7H, s), 4.35 (2H, s),<br>3.60 (2H, s), 1.41 (18H, s),<br>(CD₃OD) | 202.5–203.5<br>(decomposition) |
| 76 | 7.06 (2H, d, J = 8.8Hz),<br>6.97 (2H, s),<br>6.83 (2H, d, J = 8.8Hz),<br>5.50 (1H, brs), 4.99 (1H, s),<br>3.48 (2H, s), 1.43 (18H, s)<br>(CDCl₃) | 129–130 |
| 77 | 7.41 (5H, S),<br>7.13 (2H, d, J = 9.2Hz),<br>6.98 (2H, s),<br>6.93 (2H, d, J = 9.2Hz),<br>4.48 (2H, s), 1.41 (18H, s)<br>(CD₃OD) | 235–236<br>(decomposition) |
| 78 | 7.47 (2H, d, J = 9.1Hz),<br>7.23 (2H, d, J = 9.1Hz),<br>7.11 (2H, s),<br>3.33 (2H, t, J = 7.7Hz),<br>1.31–1.91 (6H, m),<br>1.41 (18H, s),<br>0.93 (3H, t, J = 6.5Hz)<br>(CD₃OD) | 238.5–239.5<br>(decomposition) |

EXAMPLES 79–97

Following the general procedure of Example 52 and using appropriate starting materials, the compounds listed in Table 4 below as Compounds 79–97 were prepared.

Table 4 shows the properties of the resulting compounds.

TABLE 4

Structure: HO-phenyl with $R^{1e}$, $R^{2e}$, $R^{3e}$ substituents, linked via NH to a second phenyl ring with positions 2,3,4,5,6 bearing $R^{4e}$, $R^{5e}$, $R^{6e}$.

| Compound No. | Structure | $^1$H—NMR (δ, ppm, Internal Standard: TMS) | Melting point (°C.) |
|---|---|---|---|
| 79 | $R^{1e}=R^{2e}=R^{3e}=CH_3$<br>$R^{4e}=R^{5e}=R^{6e}=H$<br>(hydrochloride) | 2.01 (3H, s), 2.12 (6H, s),<br>6.43–6.83 (4H, m),<br>6.91–7.19 (2H, m)<br>(DMSO—$d_6$) | 204–205<br>(decomposition) |
| 80 | $R^{1e}=CH_3$<br>$R^{2e}+R^{3e}=(CH_2)_4$<br>$R^{4e}=R^{5e}=R^{6e}=H$<br>(hydrochloride) | 1.60–1.68 (4H, m), 2.10 (3H, s),<br>2.45–2.51 (2H, m),<br>2.56–2.61 (2H, m),<br>6.54–6.60 (3H, m),<br>6.73 (1H, s),<br>7.02–7.08 (2H, m)<br>(DMSO—$d_6$) | 215–216<br>(decomposition) |
| 81 | $R^{1e}=R^{2e}=R^{3e}=CH_3$<br>$R^{4e}=R^{5e}=H$<br>$R^{6e}=$4-$CH_3$<br>(benzenesulfonafe) | 1.98 (3H, s), 2.11 (6H, s),<br>2.14 (3H, s),<br>6.44 (2H, d, J=8.2Hz),<br>6.68 (1H, s),<br>6.87 (1H, d, J=8.2Hz),<br>7.30–7.34 (3H, m),<br>7.58–7.62 (2H, m)<br>(DMSO—$d_6$) | 215–216<br>(decomposition) |
| 82 | $R^{1e}=R^{2e}=R^{3e}=CH_3$<br>$R^{4e}=R^{5e}=H$<br>$R^{6e}=$2-$COOCH_3$ | 2.11 (3H, s), 2.21 (6H, s),<br>3.90 (3H, s), 4.65 (1H, s),<br>6.51 (1H, ddd, J=8.0, 7.0,<br>1.1Hz), 6.63 (1H, dd, J=7.0,<br>1.1Hz), 6.87 (1H, s), 7.19 (1H,<br>ddd, J=8.0, 7.0, 1.4Hz),<br>7.92 (1H, dd, J=7.0Hz, 1.4Hz)<br>(CDCl$_3$) | 147.5–148<br>(decomposition) |
| 83 | $R^{1e}=R^{2e}=R^{3e}=CH_3$<br>$R^{4e}=R^{5e}=H$<br>$R^{6e}=$3-$COOC_2H_5$<br>(hydrochloride) | 1.27 (3H, t, J=7.1Hz),<br>1.99 (3H, s),<br>2.13 (6H, s),<br>4.25 (2H, J=7.1Hz),<br>6.69–6.72 (2H, m),<br>7.14–7.17 (3H, m)<br>(DMSO—$d_6$) | 180–181<br>(decomposition) |
| 84 | $R^{1e}=R^{2e}=R^{3e}=CH_3$<br>$R^{4e}=R^{5e}=H$<br>$R^{6e}=$4-$COOC_2H_5$ | 1.27 (3H, t, J=7.3Hz),<br>1.99 (3H, s),<br>2.14 (6H, s),<br>4.20 (2H, q, J=7.3Hz),<br>6.49 (2H, d, J=8.7Hz),<br>6.74 (1H, s),<br>7.67 (2H, d, J=8.7Hz)<br>(DMSO—$d_6$) | 149–150 |
| 85 | $R^{1e}=R^{2e}=R^{3e}=CH_3$<br>$R^{4e}=R^{5e}=H$<br>$R^{6e}=$3-$CH_2COOCH_3$ | 2.12 (3H, s), 2.20 (3H, s),<br>2.21 (3H, s), 3.52 (2H, s),<br>3.68 (3H, s), 6.53 (1H, d,<br>J=7.8Hz), 6.56 (1H, s),<br>6.66 (1H, d, J=7.8Hz),<br>6.87 (1H, s),<br>7.10 (1H, t, J=7.8Hz)<br>(CDCl$_3$) | 74–75<br>(decomposition) |
| 86 | $R^{1e}=R^{2e}=R^{3e}=CH_3$<br>$R^{4e}=R^{5e}=H$<br>$R^{6e}=$4-$CH_2COOCH_3$ | 2.11 (3H, s), 2.20 (6H, s),<br>3.50 (2H, s), 3.67 (3H, s),<br>4.64 (1H, br),<br>6.56 (2H, d, J=8.6Hz),<br>6.83 (1H, s),<br>7.05 (2H, d, J=8.6Hz)<br>(CDCl$_3$) | 110–111 |
| 87 | $R^{1e}=CH_3$<br>$R^{2e}+R^{3e}=(CH_2)_4$<br>$R^{4e}=R^{5e}=H$<br>$R^{6e}=$4-$CH_2COOCH_3$<br>(hydrochloride) | 1.58–1.68 (4H, m),<br>2.44–2.49 (2H, m),<br>2.56–2.60 (2H, m),<br>3.46 (2H, s), 3.58 (3H, s),<br>6.53 (2H, d, J=8.6Hz),<br>6.71 (1H, s),<br>6.94 (2H, d, J=8.6Hz)<br>(DMSO—$d_6$) | >151<br>(decomposition) |
| 88 | $R^{1e}=R^{2e}=(CH_3)_3C$<br>$R^{3e}=R^{4e}=R^{5e}=H$<br>$R^{6e}=$2-$CONH_2$ | 1.43 (18H, s), 6.64 (1H, ddd,<br>J=7.9, 7.9, 1.5Hz),<br>7.05 (2H, s), 7.05 (1H, dd,<br>J=7.9, 1.5Hz), 7.23 (1H,<br>ddd, J=7.9, 7.9, 1.5Hz), | 192–193 |

TABLE 4-continued (structure: HO-phenyl with R¹ᵉ, R²ᵉ, R³ᵉ substituents, linked via NH to another phenyl with positions 2,3,4,5,6 bearing R⁴ᵉ, R⁵ᵉ, R⁶ᵉ)

| Compound No. | Structure | ¹H—NMR (δ, ppm, Internal Standard: TMS) | Melting point (°C.) |
|---|---|---|---|
| 89 | R¹ᵉ=R²ᵉ=(CH₃)₃C<br>R³ᵉ=R⁴ᵉ=R⁵ᵉ=H<br>R⁶ᵉ=3-CONH₂ | 7.43 (1H, dd, J=7.9, 1.5Hz)<br>(CDCl₃)<br>1.43 (18H, s), 7.00 (2H, s),<br>7.02 (1H, ddd, J=7.8, 1.6, 1.6Hz), 7.14 (1H, ddd, J=7.8, 1.6, 1.6Hz), 7.24 (1H, dd, J=7.8, 7.8Hz),<br>7.35 (1H, dd, J=7.8, 1.6Hz)<br>(CDCl₃) | 179–180 |
| 90 | R¹ᵉ=R²ᵉ=(CH₃)₃C<br>R³ᵉ=R⁴ᵉ=R⁵ᵉ=H<br>R⁶ᵉ=4-CONH₂ | 1.43 (18H, s),<br>6.83 (2H, J=8.6Hz),<br>7.02 (2H, s),<br>7.67 (2H, d, J=8.6Hz)<br>(CDCl₃) | 211–212<br>(decomposition) |
| 91 | R¹ᵉ=R²ᵉ=R³ᵉ=CH₃<br>R⁴ᵉ=R⁵ᵉ=H<br>R⁶ᵉ=4-OCH₃<br>(benzenesulfonate) | 1.99 (3H, s), 2.10 (3H, s),<br>2.11 (3H, s), 3.64 (3H, s),<br>6.56 (2H, d, J=9.1Hz),<br>6.69 (2H, d, J=9.1Hz),<br>6.74 (1H, s), 7.30–7.33 (3H, m),<br>7.58–7.62 (2H, m)<br>(DMSO—d₆) | 234–236<br>(decomposition) |
| 92 | R¹ᵉ=R²ᵉ=(CH₃)₃C<br>R³ᵉ=R⁴ᵉ=R⁵ᵉ=H<br>R⁶ᵉ=4-SO₂CH₃ | 1.44 (18H, s),<br>3.01 (3H, s),<br>5.15 (1H, s),<br>6.84 (2H, d, J=8.9Hz),<br>7.02 (2H, s),<br>7.69 (2H, d, J=8.9Hz)<br>(CDCl₃) | 220–222 |
| 93 | R¹ᵉ=R²ᵉ=(CH₃)₃C<br>R³ᵉ=R⁴ᵉ=R⁵ᵉ=H<br>R⁶ᵉ=4-SO₂NH₂ | 1.43 (18H, s),<br>4.79 (2H, brs),<br>5.13 (1H, s),<br>6.82 (2H, dd, J=6.9, 2.0Hz),<br>7.01 (2H, s),<br>7.71 (2H, dd, J=6.9, 2.0Hz)<br>(CDCl₃) | 165–166 |
| 94 | R¹ᵉ=R²ᵉ=R³ᵉ=CH₃<br>R⁴ᵉ=R⁵ᵉ=H<br>R⁶ᵉ=4-Cl<br>(benzenesulfonate) | 1.98 (3H, s), 2.11 (6H, s),<br>6.47 (2H, d, J=8.8Hz),<br>6.70 (1H, s),<br>7.06 (2H, d, J=8.8Hz),<br>7.30–7.32 (3H, m),<br>7.58–7.62 (2H, m)<br>(DMSO—d₆) | 233–224<br>(decomposition) |
| 95 | R¹ᵉ=R²ᵉ=(CH₃)₃C<br>R³ᵉ=R⁴ᵉ=H<br>R⁵ᵉ=3-Cl, R⁶ᵉ=4-Cl | 1.42 (18H, s), 5.02 (1H, s),<br>5.45 (1H, brs),<br>6.63 (1H, dd, J=9.1, 2.4Hz),<br>6.91 (1H, d, J=2.4Hz),<br>6.92 (2H, s),<br>7.17 (1H, d, J=9.1Hz)<br>(CDCl₃) | 161.5–162 |
| 96 | R¹ᵉ=R²ᵉ=R³ᵉ=CH₃<br>R⁴ᵉ=H<br>R⁵ᵉ=3-Cl, R⁶ᵉ=4-Cl<br>(benzenesulfonate) | 1.98 (3H, s), 2.12 (6H, s),<br>6.44 (1H, dd, J=8.7, 2.6Hz),<br>6.56 (1H, d, J=2.6Hz),<br>6.71 (1H, s), 7.23 (1H, d, J=8.7Hz), 7.30–7.34 (3H, m),<br>7.58–7.62 (2H, m),<br>(DMSO—d₆) | 205–207<br>(decomposition) |
| 97 | R¹ᵉ=R²ᵉ=(CH₃)₃C<br>R³ᵉ=R⁴ᵉ=R⁵ᵉ=H<br>R⁶ᵉ=4-NO₂ | 1.44 (18H, s), 5.19 (1H, s),<br>6.11 (1H, brs),<br>6.75 (2H, dd, J=7.1, 2.1Hz),<br>7.03 (2H, s),<br>8.09 (2H, dd, J=7.1, 2.1Hz)<br>(CDCl₃) | 179–180 |

EXAMPLE 98

Preparation of 2,6-di-tert-butyl-4-(3-hydroxy-4-methoxyphenylamino)phenol hydrochloride (Compound 98)

Following the general procedure of Example 1 and using an appropriate starting material, the title compound was prepared.

M.p.: >190° C. (decomposition).

$^1$H-NMR spectrum (DMSO-$d_6$): $\delta$1.37(s,18H), 3.71 (s, 3H), 6.54 (d, J=3 Hz, 1H), 6.68 (dd, J=8 Hz, 3 Hz, 1H), 6.85 (d,J=8 Hz, 1H), 7.02 (s, 2H).

EXAMPLE 99

Preparation of 2,6-di-tert-butyl-4-(3-carboxy-4-chlorophenylamino)-phenol hydrochloride (Compound 99)

Following the general procedure of Example 24 and using an appropriate starting material, the title compound was prepared.

M.p.: 199°–201° C. (decomposition).

$^1$H-NMR spectrum (DMSO-$d_6$): $\delta$1.37 (s, 18H), 6.88 (s, 2H), 6.96 (dd, J=10 Hz, 3 Hz, 1H), 7.23 (d, J=10 Hz, 1H), 7.32 (d, J=3Hz, 1H).

EXAMPLE 100

Preparation of 4-(4-carboxymethylphenylamino)-2,3,6-trimethylphenol hydrochloride (Compound 100)

A mixture of 2.0 g of 4-(4-methoxycarbonylmethylphenylamino)-2,3,6-trimethylphenol (Compound 86), 7.2 ml of 36% hydrochloric acid and 14.2 ml of acetic acid was heated at 50° C. for 14.5 hours. The reaction mixture was cooled to room temperature, and the crystals that precipitated were filtered, washed with acetonitrile and dried, giving 1.6 g of the title compound. The filtrate was concentrated under reduced pressure, and the solid thus obtained was treated similarly, additionally giving 0.4 g of the title compound.

Table 5 shows the properties of the resulting compound.

EXAMPLE 101-104

Preparation of Compounds 101-104

Following the general procedure of Example 100 above and using appropriate starting materials, the compounds as listed in Table 5 as Compounds 101-104 were prepared. Table 5 also shows the properties of the resulting comounds.

TABLE 5

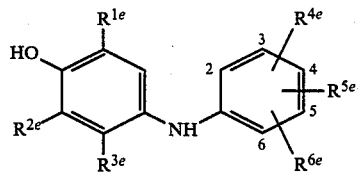

| Compound No. | Structure | $^1$H—NMR ($\delta$, ppm, Internal Standard: TMS) | Melting point (°C.) |
|---|---|---|---|
| 100 | $R^{1e}=R^{2e}=R^{3e}=CH_3$<br>$R^{4e}=R^{5e}=H$<br>$R^{6e}=$4-$CH_2COOH$<br>(hydrochloride) | 2.00 (3H, s),<br>2.12 (6H, s),<br>3.36 (2H, s),<br>6.51 (2H, d, J=8.6Hz),<br>6.74 (1H, s),<br>6.96 (2H, d, J=8.6Hz),<br>(DMSO—$d_6$) | 215.5–216 (decomposition) |
| 101 | $R^{1e}=R^{2e}=R^{3e}=CH_3$<br>$R^{4e}=R^{5e}=H$<br>$R^{6e}=$3-COOH<br>(hydrochloride) | 2.00 (3H, s),<br>2.14 (6H, s),<br>6.60–6.84 (2H, m),<br>7.00–7.20 (3H, m),<br>(DMSO—$d_6$) | 221.5–222.5 (decomposition) |
| 102 | $R^{1e}=R^{2e}=R^{3e}=CH_3$<br>$R^{4e}=R^{5e}=H$<br>$R^{6e}=$4-COOH<br>(hydrochloride) | 2.00 (3H, s),<br>2.14 (6H, s),<br>6.49 (2H, d, J=8.7Hz),<br>6.74 (1H, s),<br>7.65 (2H, d, J=8.7Hz)<br>(DMSO—$d_6$) | 199.5–200.5 (decomposition) |
| 103 | $R^{1e}=R^{2e}=R^{3e}=CH_3$<br>$R^{4e}=R^{5e}=H$<br>$R^{6e}=$3-$CH_2COOH$<br>(hydrochloride) | 1.99 (3H, s), 2.11 (6H, s),<br>3.36 (2H, s),<br>6.35–6.38 (1H, m),<br>6.44–6.47 (2H, m),<br>6.71 (1H, s),<br>6.97 (1H, dd, J=7.7, 7.7Hz)<br>(DMSO—$d_6$) | >195 (decomposition) |
| 104 | $R^{1e}=CH_3$<br>$R^{2e}+R^{3e}=(CH_2)_4$<br>$R^{4e}=R^{5e}=H$<br>$R^{6e}=$4-$CH_2COOH$<br>(hydrochloride) | 1.52–1.73 (4H, m),<br>2.10 (3H, s),<br>2.47–2.49 (2H, m),<br>2.56–2.60 (2H, m),<br>3.36 (2H, s),<br>6.53 (2H, d, J=8.5Hz),<br>6.71 (1H, s),<br>6.94 (2H, d, J=8.5Hz)<br>(DMSO—$d_6$) | 202–204 (decomposition) |

Some of the compounds of the present invention were subjected to pharmacological tests with the following results (1) Anti-inflammatory activity:inhibition of carrageenin-induced paw edema in rats The compound was tested for the above activity according to the method of Winter et al. [Proc. Soc. Exp. Biol. Med. 111, 544 (1962)] using male rats of S.D. strain (170 to 190 g, fasted), five rates in each group.

One hour after the test compound was orally given to the animal, 0.1 ml of 1% carrageenin solution was subcutaneously injected into the right footpad. The paw volume was measured 3 hours thereafter, and the resulting increase in the volume was calculated based on the volume before the injection of carrageenin solution. The percent inhibition was determined in comparison with the increase in the control group.

Table 6 below shows the results.

TABLE 6

| Compound No. | Percent inhibition of edema (%) (100 mg/kg p.o.) |
|---|---|
| 1 | 57 |
| 2 | 12 |
| 3 | 25 |
| 4 | 16 |
| 7 | 41 |
| 12 | 41 |
| 14 | 42 |
| 28 | 58 |
| 31 | 33 |
| 32 | 74 |
| 38 | 79 |
| 48 | 62 |
| 51 | 10 |
| 63 | 29 |
| 66 | 15 |
| 71 | 20 |
| 76 | 47 |
| 79 | 47 |
| 89 | 31 |
| 92 | 35 |
| 93 | 16 |
| 2,6-di-tert-butyl-4-phenylaminophenol | 62 |
| indomethacin | 62 (5 mg/kg p.o.) |

(2) 5-Lipoxygenase inhibitory activity

Cells were prepared and 5-lipoxygenase activity was determined according to the method of Bokoch et al. (J. Biol. Chem., 256, 4156 (1981)) and to the method of Ochi et al. (J. Biol. Chem., 258, 5754 (1983)).

More specifically, 2% casein was intraperitoneally given to a guinea pig, which was bleeded to death 14 to 16 hours thereafter. The peritoneal cavity was washed to collect exudate cells, which were suspended in a phosphate buffer containing 1 mM $CaCl_2$ and 5.5 mM glucose to a concentration of $2.5 \times 10^7$ cells/ml. The cell suspension was incubated at 30° C. for 2 minutes. The test compound was then added to the cell suspension, followed by incubation for 2 minutes. With addition of 10 μM of A23187 first and then 10 μM of $^{14}C$-arachidonic acid to the resulting suspension. Then, the suspension was incubated for 3 minutes. Citric acid (0.2 M) was thereafter added to the suspension to stop the reaction, the product was extracted with ethyl acetate, and the extract was spotted on a silica gel plate and developed. The arachidonic acid, 5(S)-hydroxy-6,8,11,14-eicosatetraenoic acid (5-HETE) and other portions were thereafter scraped off, and $^{14}C$ was counted by a scintillator. The inhibitory activity of the test compound was expressed in terms of percent inhibition relative to the ratio of formation of 5-HETE in a control group.

Table 7 shows the results.

TABLE 7

| Compound No. | Percent inhibition of 5-lipoxygenase (%) | |
|---|---|---|
| | (1 μM) | (10 μM) |
| 1 | 24 | 36 |
| 5 | 21 | 46 |
| 7 | — | 49 |
| 9 | 27 | 67 |
| 14 | 15 | 57 |
| 19 | 37 | 58 |
| 20 | 16 | 51 |
| 22 | 28 | 67 |
| 24 | 26 | 51 |
| 25 | — | 66 |
| 26 | 33 | 71 |
| 29 | 19 | 71 |
| 31 | 50 | 88 |
| 32 | 34 | 63 |
| 33 | 52 | 86 |
| 42 | 19 | 50 |
| 52 | 75 | 95 |
| 79 | 87 | 93 |
| 80 | 78 | 94 |
| 81 | 91 | 95 |
| 86 | 93 | 92 |
| 87 | 89 | 95 |
| 91 | 95 | 95 |
| 94 | 90 | 96 |
| 102 | 42 | 90 |
| 103 | 41 | 91 |
| 104 | 55 | 90 |
| 2,6-di-tert-butyl-4-phenylaminophenol | 2 | 62 |
| NDGA | 45 | — |

In Table 7, "NDGA" stands for nordihydroguaiaretic acid.

PREPARATION EXAMPLE 1

| Compound 38 | 200 mg |
|---|---|
| Glucose | 250 mg |
| Distilled water for injection | Adequate amount |
| Total | 5 ml |

In the distilled water for injection was dissolved the Compound 38 and glucose, and the resulting solution was placed in a 5 ml ampoule. The air in the ampoule was replaced by nitrogen gas. The preparation was sterilized by heating at 121° C. for 15 minutes, giving an injection solution having the above composition.

PREPARATION EXAMPLE 2

| Compound 38 | 100 g |
|---|---|
| Crystalline cellulose (Trademark "Avicel PH101" product of Asahi Chemical Industry Co., Ltd., Japan) | 40 g |
| Corn starch | 30 g |
| Magnesium stearate | 2 g |
| Total | 172 g |
| Hydroxypropyl methyl cellulose (Trademark "TC-5", product of Shin-etsu Kagaku Kogyo Kabushiki Kaisha, Japan) | 10 g |
| Polyethylene glycol 6000 | 3 g |
| Pigment | 0.3 g |
| Titanium oxide | 0.2 g |
| Water | 86.5 g |

-continued

| | |
|---|---|
| Total | 100 g |

The foregoing Compound 38, Crystalline cellulose, Corn starch and magnesium stearate were ground and formulated into tablets with use of sugar-coated punch having a radius of 8 mm. The resulting tablets were coated with a film coating agent consisting of hydroxypropyl methyl cellulose, polyethylene glycol 6000, castor oil and ethanol, giving film-coated tablets having the above composition.

PREPARATION EXAMPLE 3

| | |
|---|---|
| Compound 91 | 2 g |
| Purified lanolin | 5 g |
| Bleached bees wax | 5 g |
| White petrolatum | 88 g |
| Total | 100 g |

The bleached bees wax was melted by heating, and thereto were added Compound 91, purified lanolin and white petrolatum. The mixture was heated until it became liquid, and then stirred until it solidified, giving an ointment having the above composition.

We claim:
1. A compound selected from the group consisting of:
(1) a compound of the formula

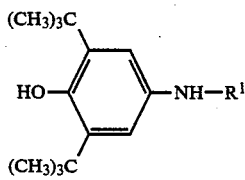
(1)

wherein $R^1$ represents a phenyl group having 1-3 substituents selected from the class consisting of cyano group, carbamoyl group, nitro group, sulfamoyl group, hydroxy-$C_1$-$C_6$ alkyl group, $C_1$-$C_6$-alkyoxycarbonyl-Cl-$C_6$ alkyl group, carboxy-$C_1$-$C_6$ alkyl group, $C_1$-$C_6$ haloalkyl group, $C_1$-$C_6$ alkylthio group, phenylthio group ad $C_1$-$C_6$ alkysulfonyl group, and a salt thereof;
(2) a compound of the formula

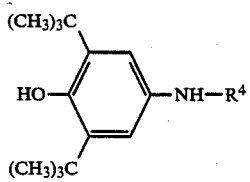
(2)

wherein $R^2$ and $R^3$ are as defined above and $R^4$ represents a tri($C_1$-$C_6$ alkoxy) phenyl group, dihalophenyl group or a group of the formula

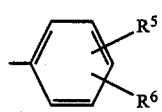

wherein $R^5$ is hydroxy-$C_1$-$C_6$ alkyl or carboxyl-$C_1$-$C_6$ alkyl group and $R_6$ is hydroxyl group, halogen atom or $C_1$-$C_6$ alkyl group, and a salt thereof;
(3) a compound of the formula

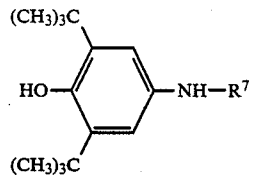
(3)

wherein $R^7$ represents a phenyl group having a substituent selected from the class consisting of fluoro, 2-chloro, $C_1$-$C_6$ alkoxy, carboxyl, n-butyl, amino, hydroxyl and N,N-di($C_1$-$C_6$ alkyl) amino groups, or $R^7$ represents a phenyl group having carboxyl and $C_1$-$C_6$ alkyl groups as the substituent, a phenyl group having carboxyl and hydroxyl groups as the substituent, a phenyl group having carboxyl group and halogen atom as the substituent, a phenyl group having hydroxyl group and halogen atom as the substituent, or a phenyl group having $C_1$-$C_6$ alkoxy and hydroxy group as the substituent, and a salt thereof; and
(4) a compound of the formula

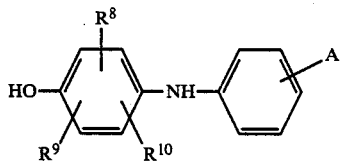
(4)

wherein $R^8$ and $R^9$ are the same and each represent tertbutyl group, $R^{10}$ represents hydrogen atom or $C_1$-$C_6$ alkyl group, or $R^9$ and $R^{10}$, taken together with the phenyl ring to which they are attached, form a fused ring of the formula

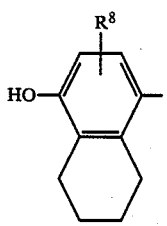

and A represents:
a hydrogen atom,
$C_1$-$C_6$ alkylsulfonyl group,
$C_1$-$C_6$ alkoxycarbonyl group,
piperidinocarbonyl group,
phenyl-$C_1$-$C_6$ alkylcarbamoyl group,
$C_1$-$C_{12}$ alkylcarbamoyl group,
$C_3$-$C_8$ cycloalkylcarbamoyl group,
$C_2$-$C_6$ alkenyl group having a substituent selected from the class consisting of $C_1$-$C_6$ alkoxy-carbonyl, carboxyl, $C_1$-$C_6$ acyl, $C_1$-$C_6$ alkylcarbamoyl and $C_3$-$C_8$ cycloalkylcarbamoyl groups,
$C_1$-$C_6$ alkyl group having a substituent selected from the class consisting of $C_3$-$C_8$ cycloalkylcarbamoyl, $C_1$-$C_6$ alkylcarbamoyl, phenyl-$C_1$-$C_6$ alkyl-carbamoyl, piperidinocarbonyl, morpholinocarbonyl and hydrazinocarbonyl groups,
carboxy-$C_1$-$C_6$ alkyl group,
$C_1$-$C_6$ alkoxycarbonyl-$C_1$-$C_6$ alkyl group,
$C_1$-$C_6$ alkyl group,
carboxyl group,
$C_1$-$C_6$ alkoxy group,
halogen atom, or
a group —$NR^{11}R^{12}$, wherein $R^{11}$ is hydrogen atom or $C_1$-$C_6$ alkyl group, and $R^{12}$ is $C_1$-$C_6$ alkyl group having a phenyl group as the substituent, phenyl group, benzoyl group which may optionally have $C_1$-$C_6$ alkyl group as the substituent, $C_1$-$C_6$ acyl group which may optionally have $C_1$-$C_6$ alkoxycarbonyl group as the substituent, $C_1$-$C_6$ alkylsulfonyl group or phenylsulfonyl group; with the proviso that when $R^{10}$ is hydrogen atom, the group A does not represent hydrogen atom, carboxy-$C_1$-$C_6$ alkyl group, $C_1$-$C_6$ alkoxycarbonyl-$C_1$-$C_6$ alkyl group, $C_1$-$C_6$ alkyl group, carboxyl group, $C_1$-$C_6$ alkoxy group or halogen atom; and a salt thereof.

2. A compound as defined in claim 1 which is selected from the group consisting of:
(1) a compound of the formula (1) wherein $R^1$ is a phenyl group having cyano or hydroxy-$C_1$-$C_6$ alkyl group as the substituent,
(2) a compound of the formula (2) wherein $R^6$ is a halogen atom,
(3) a compound of the formula (3) wherein $R^7$ is a fluorophenyl group, and
(4) a compound of the formula (4) wherein A is a hydrogen atom, $C_2$-$C_6$ alkenyl group having a carboxyl or $C_1$-$C_6$ alkoxy group, $C_1$-$C_6$ alkoxycarbonyl-$C_1$-$C_6$ alkyl group, $C_1$-$C_6$ alkyl group or halogen atom.

3. A compound as defined in claim 1 which is selected from the group consisting of:
2,6-di-tert-butyl-4-(4-chloro-2-hydroxymethylphenylamino)phenol,
2,6-di-tert-butyl-4-(2-hydroxymethylphenylamino)phenol,
2-(3,5-di-tert-butyl-4-hydroxyphenylamino)cinnamic acid,
2,6-di-tert-butyl-4-(4-cyanophenylamino)phenol,
2,6-di-tert-butyl-4-(4-fluorophenylamino)phenol,
2-methyl-4-phenylamino-5,6,7,8-tetrahydronaphthol, and
2-methyl-4-(4-methoxycarbonylmethylphenylamino)-5,6,7,8-tetrahydrohaphthol.

4. An anti-inflammatory composition comprising an effective amount of at least one compound as defined in claim 1 in admixture with a pharmaceutically acceptable carrier.

5. A pharmaceutical composition for inhibiting lipoxygenase comprising an effective amount of at least one compound as defined in claim 1 in admixture with a pharmaceutically acceptable carrier.

6. A method for treating inflammation in a patient comprising administering to said patient an effective amount of at least one compound selected from the group consisting of:
(a) a compound of the formula

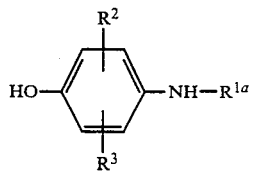

wherein $R^{1a}$ represents unsubstituted phenyl group or a phenyl group having 1-3 substituents selected from the class consisting of cyano group, carbamoyl group, nitro group, sulfamoyl group, hydroxy-$C_1$-$C_6$ alkyl group, $C_1$-$C_6$ alkoxycarbonyl-$C_1$-$C_6$ alkyl group, carboxy-$C_1$-$C_6$ alkyl group, $C_1$-$C_6$ haloalkyl group, $C_1$-$C_6$ acyl group, $C_1$-$C_6$ alkylthio group, phenylthio group, $C_1$-$C_6$ alkylsulfonyl group, amino group, $C_1$-$C_6$ alkoxy group, hydroxyl group, $C_1$-$C_6$ alkyl group and halogen atom, and $R^2$ and $R^3$ are the same or different and represent $C_1$-$C_6$ alkyl group and a salt thereof; and
(b) a compound of the formula

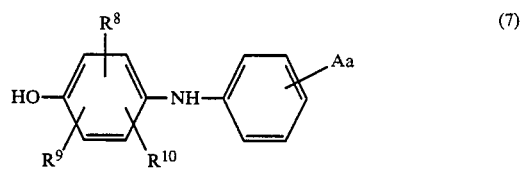

wherein $R^8$, $R^9$ and $R^{10}$ are as defined in the formula (4) above, and Aa represents:
a hydrogen atom,
$C_1$-$C_6$ alkylsulfonyl group,
$C_1$-$C_6$ alkoxycarbonyl group,
piperidinocarbonyl group,
phenyl-$C_1$-$C_6$ alkylcarbamoyl group,
$C_1$-$C_{12}$ alkylcarbamoyl group,
$C_3$-$C_8$ cycloalkylcarbamoyl group,
$C_2$-$C_6$ alkenyl group having a substituent selected from the class consisting of $C_1$-$C_6$ alkoxycarbonyl, carboxyl, $C_1$-$C_6$ acyl, $C_1$-$C_6$ alkylcarbamoyl and $C_3$-$C_8$ cycloalkylcarbamoyl groups,
$C_1$-$C_6$ alkyl group having a substituent selected from the class consisting of $C_3$-$C_8$ cycloalkylcarbamoyl, $C_1$-$C_6$ alkylcarbamoyl, phenyl-$C_1$-$C_6$ alkylcarbamoyl, piperidinocarbonyl, morpholinocarbonyl and hydrazinocarbonyl groups,
carboxy-$C_1$-$C_6$ alkyl group,
$C_1$-$C_6$ alkoxycarbonyl-$C_1$-$C_6$ alkyl group,
$C_1$-$C_6$ alkyl group,
carboxy group,
$C_1$-$C_6$ alkoxy group,
halogen atom, or
a group —$NR^{11}R^{12a}$ (wherein $R^{11}$ is hydrogen atom or $C_1$-$C_6$ alkyl group, and $R^{12a}$ is $C_1$-$C_6$ alkyl group, $C_1$-$C_6$ alkyl group having a phenyl group as the substituent, phenyl group, benzoyl group which may optionally have $C_1$-$C_6$ alkyl as the substituent, $C_1$-$C_6$ acyl group which may optionally have $C_1$-$C_6$ alkoxycarbonyl group as the substituent, $C_1$-$C_6$ alkylsulfonyl group or phenylsulfonyl group); with the proviso that when $R^{10}$ is hydrogen atom, the group Aa does not represent hydrogen atom, carboxy-$C_1$-$C_6$ alkyl group, $C_1$-$C_6$ alkoxycarbonyl-$C_1$-$C_6$ alkyl group, $C_1$-$C_6$ alkyl group, carboxyl group, $C_1$–$C_6$ alkoxy group or halogen atom, and a salt thereof.

7. A method as defined in claim 6 wherein the compound is selected from the group consisting of:
   (a) a compound of the formula (5) wherein $R^{1a}$ is unsubstituted phenyl group, phenyl group having a halogen atom and hydroxy-$C_1$–$C_6$ alkyl group as the substituent, phenyl group having hydroxy-$C_1$–$C_6$ alkyl group as the substituent, cyanophenyl group or halophenyl group and $R^2$ and $R^3$ are the same or different and each represent $C_1$–$C_6$ alkyl group, and
   (b) a compound of the formula (7) wherein $R^8$, $R^9$ and $R^{10}$ are as defined in the formula (7) and Aa is $C_2$–$C_6$ alkenyl group having carboxyl group as the substituent.

8. A method as defined in claim 6 wherein the compound is selected from the group consisting of:
2,6-di-tert-butyl-4-(4-chloro-2-hydroxymethyl-phenylamino)phenol,
2,6-di-tert-butyl-4-(2-hydroxymethylphenylamino)-phenol,
2-(3,5-di-tert-butyl-4-hydroxyphenylamino)cinnamic acid,
2,6-di-tert-butyl-4-(4-cyanophenylamino)phenol,
2,6-di-tert-butyl-4-(4-fluorophenylamino)phenol and
2,6-di-tert-butyl-4-phenylaminophenol.

9. A method for inhibiting lipoxygenase in a patient comprising administering to said patient an effective amount of at least one compound selected from the group consisting of:
   (a) a compound of the formula

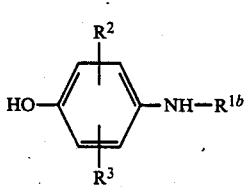

(6)

wherein $R^{1b}$ represents unsubstituted phenyl group or a phenyl group having 1–3 substituents selected from the class consisting of carboxyl group, cyano group, carbamoyl group, nitro group, sulfamoyl group, hydroxy-$C_1$–$C_6$ alkyl group, $C_1$–$C_6$ alkoxycarbonyl $C_1$–$C_6$-alkyl group, carboxy-$C_1$–$C_6$ alkyl group, $C_1$–$C_6$ haloalkyl group, $C_1$–$C_6$ acyl group, $C_1$–$C_6$ alkylthio group, phenylthio group, $C_1$–$C_6$ alkylsulfonyl group, amino group, $C_1$–$C_6$ alkoxy group, hydroxyl group, $C_1$–$C_6$ alkyl group and halogen atom, and $R^2$ and $R^3$ each are the same or different and represent $C_1$–$C_6$ alkyl group and a salt thereof; and
   (b) a compound of the formula

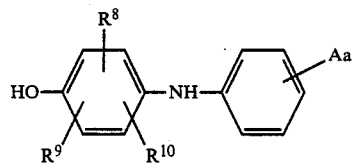

(7)

wherein $R^8$, $R^9$ and $R^{10}$ are as defined in the formula (4) above, and Aa represents:
a hydrogen atom,
$C_1$–$C_6$ alkylsulfonyl group,
$C_1$–$C_6$ alkoxycarbonyl group,
piperidinocarbonyl group,
phenyl-$C_1$–$C_6$ alkylcarbamoyl group,
$C_1$–$C_{12}$ alkylcarbamoyl group,
$C_3$–$C_8$ cycloalkylcarbamoyl group,
$C_2$–$C_6$ alkenyl group having a substituent selected from the class consisting of $C_1$–$C_6$ alkoxycarbonyl, carboxyl, $C_1$–$C_6$ acyl, $C_1$–$C_6$ alkylcarbamoyl and $C_3$–$C_8$ cycloalkylcarbamoyl groups,
$C_1$–$C_6$ alkyl group having a substituent selected from the class consisting of $C_3$–$C_8$ cycloalkylcarbamoyl, $C_1$–$C_6$ alkylcarbamoyl, phenyl-$C_1$–$C_6$ alkylcarbamoyl, piperidinocarbonyl, morpholinocarbonyl and hydrazinocarbonyl groups,
carboxy-$C_1$–$C_6$ alkyl group,
$C_1$–$C_6$ alkoxycarbonyl-$C_1$–$C_6$ alkyl group,
$C_1$–$C_6$ alkyl group,
carboxyl group,
$C_1$–$C_6$ alkoxy group,
halogen atom, or
a group —$NR^{11}R^{12a}$ (wherein $R^{11}$ is hydrogen atom or $C_1$–$C_6$ alkyl group, and $R^{12a}$ is $C_1$–$C_6$ alkyl group, $C_1$–$C_6$ alkyl group having a phenyl group as the substituent, phenyl group, benzoyl group which may optionally have $C_1$–$C_6$ alkyl group as the substituent, $C_1$–$C_6$ acyl group which may optionally have $C_1$–$C_6$ alkoxycarbonyl group as the substituent, $C_1$–$C_6$ alkylsulfonyl group or phenylsulfonyl group); with the proviso that when $R^{10}$ is hydrogen atom, the group Aa does not represent hydrogen atom, carboxy-$C_1$–$C_6$ alkyl group, $C_1$–$C_6$ alkoxycarbonyl-$C_1$–$C_6$ alkyl group, $C_1$–$C_6$ alkyl group, carboxyl group, $C_1$–$C_6$ alkoxy group or halogen atom, and a salt thereof.

10. A method as defined in claim 9 wherein the compound is a compound of the formula (7) wherein $R^8$, $R^9$ and $R^{10}$ are as defined in the formula (7) and Aa is hydrogen, $C_1$–$C_6$ alkoxy, $C_1$–$C_6$ alkoxycarbonyl-$C_1$–$C_6$ alkyl, $C_1$–$C_6$ alkyl, halogen or $C_2$–$C_6$ alkenyl having $C_1$–$C_6$ alkoxycarbonyl group as the substituent.

11. A method as defined in claim 9 wherein the compound is selected from the group consisting of:
2,3,6-trimethyl-4-(4-methoxyphenylamino)phenol,
2,3,6-trimethyl-4-(4-methoxycarbonylmethyl-phenylamino)phenol,
2,3,6-trimethyl-4-(4-methylphenylamino)phenol,
2,3,6-trimethyl-4-(4-chlorophenylamino)phenol,
2-methyl-4-phenylamino-5,6,7,8-tetrahydronaphthol,
2-methyl-4-(4-methoxycarbonylmethylphenylamino)-5,6,7,8-tetrahydronaphthol,
2,3,6-trimethyl-4-phenylaminophenol and ethyl 3-(4-hydroxy-2,3,5-trimethylphenylamino)cinnamate.

* * * * *

REEXAMINATION CERTIFICATE (1750th)

United States Patent [19]

Hashimoto et al.

[11] B1 4,906,662

[45] Certificate Issued Jul. 14, 1992

[54] PHENOL DERIVATIVES, THEIR PREPARATION AND THE USE THEREOF

[75] Inventors: Kinji Hashimoto; Kiyoto Goto; Ken-ichi Kanai, all of Naruto; Yoshiaki Tsuda, Anan, all of Japan

[73] Assignee: Otsuka Pharmaceutical Factory, Inc., Naruto, Japan

Reexamination Request:
No. 90/002,376, Jun. 24, 1991

Reexamination Certificate for:
Patent No.: 4,906,662
Issued: Mar. 6, 1990
Appl. No.: 7,044
Filed: Jan. 27, 1987

[30] Foreign Application Priority Data

Sep. 29, 1986 [JP] Japan ............................ 61-230484

[51] Int. Cl.$^5$ ............... A61K 31/195; C07C 101/34; C07C 101/72; C07C 101/44
[52] U.S. Cl. .............................. 514/524; 514/237.5; 514/319; 514/330; 514/535; 514/539; 514/561; 514/563; 514/576; 514/656; 514/657; 514/658; 544/165; 546/205; 546/221; 558/418; 562/431; 562/433; 562/453; 562/454; 562/455; 562/478; 560/16; 560/43; 560/44; 560/45; 560/48; 560/75; 564/86; 564/97; 564/150; 564/167; 564/171; 564/220; 564/221; 564/308; 564/429; 564/430; 564/433; 564/434
[58] Field of Search ............... 564/86, 97, 150, 167, 564/220, 221, 429, 433, 434; 560/45, 43; 562/453, 454; 544/165; 546/205, 221; 558/418; 514/237.5, 310, 330, 561, 563, 524, 603, 619, 657, 658

[56] References Cited

U.S. PATENT DOCUMENTS

| | | | |
|---|---|---|---|
| 4,496,590 | 1/1985 | Schlegel et al. | 514/646 |
| 4,515,980 | 5/1985 | Bailey | 560/45 |
| 4,539,429 | 9/1985 | Bailey | 514/658 |
| 4,716,178 | 12/1987 | Scherrer et al. | 514/563 |

FOREIGN PATENT DOCUMENTS

0211549 2/1987 European Pat. Off. .
0212848 4/1987 European Pat. Off. .

*Primary Examiner*—Bernard Dentz

[57] ABSTRACT

Disclosed are phenol derivatives of the formula

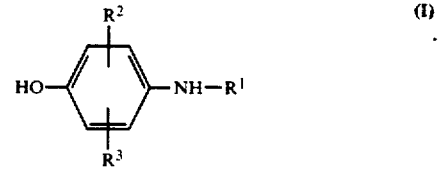

wherein $R^1$ is a substituted phenyl group, $R^2$ and $R^3$ are $C_1$-$C_6$ alkyl group and of the formula

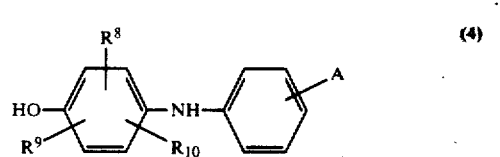

wherein $R^8$, $R^9$ and $R^{10}$ are $C_1$-$C_6$ alkyl and the like and A is H, $C_1$-$C_6$ alkylsulfonyl and the like substituents. These compounds and some related compounds have anti-inflammmatory activity and lipoxygenase inhibitory activity.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 11 is cancelled.

Claims 1-3 and 6-10 are determined to be patentable as amended.

Claims 4 and 5, dependent on an amended claim, are determined to be patentable.

1. A compound selected from the group consisting of:
(1) a compound of the formula

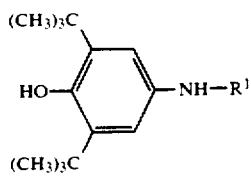

wherein $R^1$ represents a phenyl group having 1-3 substituents selected from the class consisting of cyano group, carbamoyl group, nitro group, sulfamoyl group, [hydroxy-$C_1$-$C_6$ alkyl group,] $C_1$-$C_6$-[alkyoxycarbonyl-Cl-$C_6$] *alkoxycarbonyl-$C_1$-$C_6$ alkyl group*, carboxy-$C_1$-$C_6$ alkyl group [$C_1$-$C_6$ haloalkyl group,] $C_1$-$C_6$ alkylthio group, phenylthio group [ad] *and* $C_1$-$C_6$ alkysulfonyl group, and a salt thereof;

(2) a compound of the formula

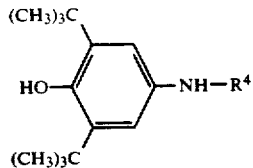

wherein [$R^2$ and $R^3$ are as defined above and] $R^4$ represents [a tri($C_1$-$C_6$ alkoxy) phenyl group, dihalophenyl group or] a group of the formula

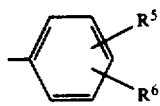

wherein $R^5$ is [hydroxy-$C_1$-$C_6$ alkyl or] carboxyl-$C_1$-$C_6$ alkyl group and $R_6$ is hydroxyl group, halogen atom or $C_1$-$C_6$ alkyl group, and a salt thereof; *and*
[(3) a compound of the formula

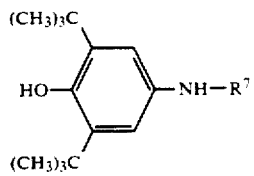

wherein $R^7$ represents a phenyl group having a substituent selected from the class consisting of fluoro, 2-chloro, $C_1$-$C_6$ alkoxy, carboxyl, n-butyl, amino, hydroxyl and N,N-di($C_1$-$C_6$ alkyl) amino groups, or $R^7$ represents a phenyl group having carboxyl and $C_1$-$C_6$ alkyl groups as the substituent, a phenyl group having carboxyl and hydroxyl groups as the substituent, a phenyl group having carboxyl group and halogen atom as the substituent, a phenyl group having hydroxyl group and halogen atom as the substituent, or a phenyl group having $C_1$-$C_6$ alkoxy and hydroxy group as the substituent, and a salt thereof; and]

(4) a compound of the formula

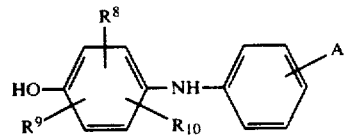

wherein $R^8$ and $R^9$ are the same and each represent tertbutyl group, $R^{10}$ represents hydrogen atom or $C_1$-$C_6$ alkyl group, or $R^9$ and $R^{10}$, taken together with the phenyl ring to which they are attached, form a fused ring of the formula

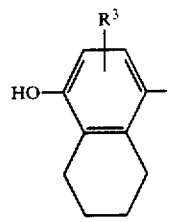

and A represents: [a hydrogen atom,] $C_1$-$C_6$ alkylsulfonyl group, [$C_1$-$C_6$ alkyoxycarbonyl group,] piperidinocarbonyl group, phenyl-$C_1$-$C_6$ alkylcarbamoyl group, $C_1$-$C_{12}$ alkylcarbamoyl group, $C_3$-$C_8$ cycloalkylcarbamoyl group, $C_2$-$C_6$ alkenyl group having a substituent selected from the class consisting of $C_1$-$C_6$ alkoxy-carbonyl, carboxyl, $C_1$-$C_6$ acyl, $C_1$-$C_6$ alkylcarbamoyl and $C_3$-$C_8$ cycloalkylcarbamoyl groups, $C_1$-$C_6$ alkyl group having a substituent selected from the class consisting of $C_3$-$C_8$ cycloalkylcarbamoyl, $C_1$-$C_6$ alkylcarbamoyl, phenyl-$C_1$-$C_6$ alkyl-carbamoyl, piperidinocarbonyl, morpholinocarbonyl and hydrazinocarbonyl groups, carboxy-$C_1$-$C_6$ alkyl group, $C_1$-$C_6$ alkoxycarbonyl-$C_1$-$C_6$ alkyl group, [$C_1$-$C_6$ alkyl group, carboxyl group, $C_1$-$C_6$ alkoxy group, halogen atom,] or a group $—NR^{11}R^{12}$, wherein $R^{11}$ is hydrogen atom or $C_1$-$C_6$ alkyl group, and $R^{12}$ is $C_1$-$C_6$ alkyl group having a phenyl group as the substituent, phenyl group, benzoyl group which may optionally have $C_1$-$C_6$ alkyl group as the substituent, [$C_1$-$C_6$ acyl group which may optionally have $C_1$-$C_6$ alkoxycarbonyl group as the substituent,] $C_1$-6 alkylsulfonyl group or phenylsulfonyl group; with the proviso that when $R^{10}$ is hydrogen atom, the group A does not represent [hydrogen atom,] carboxy-$C_1$-$C_6$ alkyl group, $C_1$-$C_6$ alkoxycarbonyl-$C_1$-$C_6$-alkyl group[,] or $c_1$-$C_6$ alkylsulfonyl group [$C_1$-$C_6$ alkyl group, carboxyl group, $C_1$-$C_6$ alkoxy group or halogen atom]; and a salt thereof.

2. A compound as defined in claim 1, which is selected from the group consisting of:
 (1) a compound of the formula (1) wherein $R^1$ is a phenyl group having cyano [or hydroxy-$C_1$-$C_6$ alkyl group] as the substituent,
 (2) a compound of the formula (2) wherein $R^6$ is a halogen atom, *and*
 [(3) a compound of the formula (3) wherein $R^7$ is a fluorophenyl group, and]
 (4) a compound of the formula (4) wherein A is [a hydrogen atom,] $C_2$-$C_6$ alkenyl group having a carboxyl *substituent* or [$C_1$-$C_6$ alkoxy group,] a $C_1$-$C_6$ alkoxycarbonyl-$C_1$-$C_6$ alkyl group[, $C_1$-$C_6$ alkyl group or halogen atom].

3. A compound as defined in claim 1, which is selected from the group consisting of:
 [2,6-di-tert-butyl-4-(4-chloro-2-hydroxymethylphenylamino)phenol, 2,6-di-tert-butyl-4-(2-hydroxymethylphenylamino)-phenol,] 2-(3,5-di-tert-butyl-4-hydroxyphenylamino)cinnamic acid[,] *and* 2,6-di-tert-butyl-4-(4-cyanophenylamino)-phenol[, 2,6-di-tert-butyl-4-(4-fluorophenylamino)phenol, 2-methyl-4-phenylamino-5,6,7,8-tetrahydronaphthol, and 2-methyl-4-(4-methoxycarbonylemethylphenylamino)-5,6,7,8-tetrahydrohaphthol,].

6. A method for treating inflammation in a patient comprising administering to said patient an effective amount of at least one compound selected from the group consisting of:
 (a) a compound of the formula

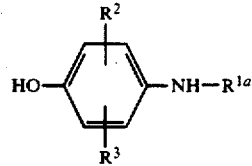

(5)

wherein $R^{1a}$ represents unsubstituted phenyl group or a phenyl group having 1-3 substituents selected from the class consisting of cyanogroup, carbamoyl group, nitro group, sulfamoyl group, [hydroxy-$C_1$-$C_6$ alkyl group,] $C_1$-$C_6$ alkoxycarbonyl-$C_1$-$C_6$ alkyl group, carboxy-$C_1$-$C_6$ alkyl group, $C_1$-$C_6$ haloalkyl group, [$C_1$-$C_6$ acyl group,] $C_1$-$C_6$ alkylthio group, phenylthio group, $C_1$-$C_6$ alkylsulfonyl group, amino group, $C_1$-$C_6$ alkoxy group, hydroxyl group, $C_1$-$C_6$ alkyl group and halogen atom, and $R^2$ and $R^3$ are the same or different and [represent] *represents* $C_1$-$C_6$ alkyl group and a salt thereof; and
 (b) a compound of the formula

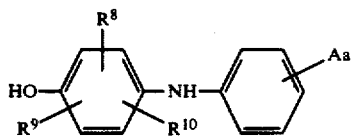

(7)

wherein $R^8$[,] *and* $R^9$ [and $R^{10}$] are [as defined in the formula (4) above] *the same and each represents* tertbutyl group, $R^{10}$ *represents hydrogen atom or $C_1$-$C_6$ alkyl group, or $R^9$ and $R^{10}$, taken together with the phenyl ring to which they are attached, form a fused ring of the formula*

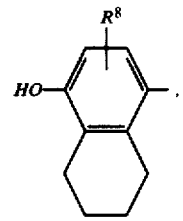

and Aa represents: a hydrogen atom, $C_1$-$C_6$ alkylsulfonyl group, [$C_1$-$C_6$ alkoxycarbonyl group,] piperidinocarbonyl group, phenyl-$C_1$-$C_6$ Alkyllcarbamoyl group, $C_1$-$C_{12}$ alkylcarbamoyl group, $C_3$-$C_8$ cycloalkylcarbamoyl group, $C_2$-$C_6$ alkenyl group having a substituent selected from the class consisting of $C_1$-$C_6$ alkoxycarbonyl, carboxyl, $C_1$-$C_6$ acyl, $C_1$-$C_6$ alkylcarbamoyl, and $C_3$-$C_8$ cycloalkylcarbamoyl groups, $C_1$-$C_6$ alkyl group having a substituent selected from the class consisting of $C_3$-$C_8$ cycloalkylcarbamoyl, $C_1$-$C_6$ alkylcarbamoyl, phenyl-$C_1$-$C_6$ alkylcarbamoyl, piperidinocarbonyl, morpholinocarbonyl and hydrazinocarbonyl groups, carboxy-$C_1$-$C_6$ alkyl group, $C_1$-$C_6$ alkoxycarbonyl-$C_1$-$C_6$ alkyl group, $C_1$-$C_6$ alkyl group, [carboxy group,] $C_1$-$C_6$ alkoxy group, halogen atom, or a group —$NR^{11}R^{12a}$ [(], wherein $R^{11}$ is hydrogen atom or $C_1$-$C_6$ alkyl group, and $R^{12a}$ is $C_1$-$C_6$ alkyl group, $C_1$-$C_6$ alkyl group having a phenyl group as the substituent, phenyl group, benzoyl group which may optionally have $C_1$-$C_6$ alkyl as the substituent, $C_1$-$C_6$ acyl group which may optionally have $C_1$-$C_6$ alkoxycarbonyl group as the substituent, $C_1$-$C_6$ alkylsulfonyl group or phenylsulfonyl group[)]; with the proviso that when $R^{10}$ is hydrogen atom, the group Aa does not represent hydrogen atom, carboxy-$C_1$-$C_6$ alkyl group, $C_1$-$C_6$ alkoxycarbonyl-$C_1$-$C_6$ alkyl group, $C_1$-$C_6$ alkyl group, $C_1$-$C_6$ *alkylsulfonyl group,* [carboxyl group,] $C_1$-$C_6$ alkoxy group or halogen atom, and a salt thereof.

7. A method as defined in claim 6 wherein the compound is selected from the group consisting of:
 (a) a compound of the formula (5) wherein $R^{1a}$ is unsubstituted phenyl group, [phenyl group having a halogen atom and hydroxy-$C_1$-$C_6$ alkyl group as the substituent, phenyl group having hydroxy-$C_1$-$C_6$ alkyl group as the substituent,] cyanophenyl group or halophenyl group and $R^2$ and $R^3$ are the same or different and each represent $C_1$-$C_6$ alkyl group, and
 (b) a compound of the formula (7) wherein $R^8$[, ] *and* $R^9$ [and $R^{10}$] are [as defined in the formula (7)] *the same and each represents tertbutyl group, $R^{10}$ represents hydrogen atom or $C_1$-$C_6$ alkyl group or $R^9$ and $R^{10}$, taken together with the phenyl ring to which they are attached, form a fused ring of the formula*

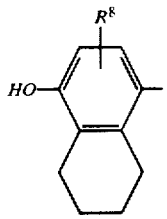

and Aa is $C_2-C_6$ alkenyl group having carboxyl group as the substituent.

8. A method as defined in claim 6 wherein the compound is selected from the group consisting of:

[2,6-di-tert-butyl-4-(4-chloro-2-hydroxymethyl-phenylamino) phenol, 2,6-di-tert-butyl-4-(2-hydroxymethylphenylamino)phenol,] 2-(3,5-di-tert-butyl-4-hydroxyphenylamino)cinnamic acid, 2,6-di-tert-butyl-4 -(4-cyanophenylamino)phenol, 2,6-di-tert-butyl-4-(4-fluorophenylamino)phenol and 2,6-di-tert-butyl-4-phenylaminophenol.

9. A method for inhibiting lipoxygenase in a patient comprising administering to said patient an effective amount of at least one compound selected from the group consisting of:

(a) a compound of the formula

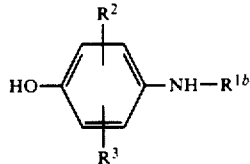

(6)

wherein $R^{1b}$ represents unsubstituted phenyl group or a phenyl group having 1-3 substituents selected from the class consisting of [carboxyl group,] cyano group, carbamoyl group, nitro group, sulfamoyl group, [hydroxy-$C_1 \alpha C_6$ alkyl group,] $C_1-C_6$ alkoxycarbonyl-$C_1-C_6$ -alkyl group, carboxy-$C_1-C_6$ alkyl group, $C_1-C_6$ haloalkyl group, [$C_1-C_6$ acyl group,] $C_1-C_6$ alkylthio group, phenylthio group, $C_1-C_6$ alkylsulfonyl group, amino group, $C_1-C_6$ alkoxy group, [hydroxyl group,] $C_1-C_6$ alkyl group and halogen atom, and $R^2$ and $R^3$ each are the same or different and represent $C_1-C_6$ alkyl group and a salt thereof; and (b) a compound of the formula

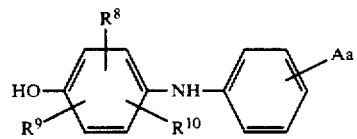

(7)

wherein $R^8$[,] and $R^9$ [and $R^{10}$] are [as defined in the formula (4) above,] the same and each represents tertbutyl group, $R^{10}$ represents hydrogen atom or $C_1-C_6$ alkyl group, or $R^9$ and $R^{10}$, taken together with the phenyl ring to which they are attached, form a fused ring of the formula

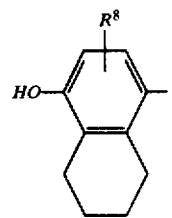

and Aa represents: a hydrogen atom, $C_1-C_6$ alkylsulfonyl group, [$C_1-C_6$ alkoxycarbonyl group,] piperidinocarbonyl group, phenyl-$C_1-C_6$ alkylcarbamoyl group, $C_1-C_{12}$ alkylcarbamoyl group, $C_3-C_8$ cycloalkylcarbamoyl group, $C_2-C_6$ alkenyl group having a substituent selected from the class consisting of $C_1-C_6$ alkoxycarbonyl, carboxyl, $C_1-C_6$ acyl, $C_1-C_6$ alkylcarbamoyl and $C_3-C_8$ cycloalkylcarbamoyl groups, $C_1-C_6$ alkyl group having a substituent selected from the class consisting of $C_3-C_8$ cycloalkylcarbamoyl, $C_1-C_6$ alkylcarbamoyl, phenyl-$C_1-C_6$ alkylcarbamoyl, piperidinocarbonyl, morpholinocarbonyl and hydrazinocarbonyl groups, carboxy-$C_1-C_6$ alkyl group, $C_1-C_6$ alkoxycarbonyl-$C_1-C_6$ alkyl group, $C_1-C_6$ alkyl group, [carboxyl group,] $C_1-C_6$ alkoxy group, halogen atom, or a group $—NR^{11}R^{12a}$ [(], wherein $R^{11}$ is hydrogen atom or $C_1-C_6$ alkyl group, and $R^{12a}$ is $C_1-C_6$ alkyl group, $C_1-C_6$ alkyl group having a phenyl group as the substituent, phenyl group, benzoyl group which may optionally have $C_1-C_6$ alkyl group as the substituent, $C_1-C_6$ acyl group which may optionally have $C_1-C_6$ alkoxycarbonyl group as the substituent, $C_1-C_6$ alkylsulfonyl group or phenylsulfonyl group[)]; with the proviso that when $R^{10}$ is hydrogen atom, the group Aa does not represent hydrogen atom, $C_1-C_6$ alkylsulfonyl group, carboxy-$C_1-C_6$ alkyl group, $C_1-C_6$ alkoxycarbonyl-$C_1-C_6$ alkyl group, $C_1-C_6$ alkyl group, $C_1-C_6$ alkyl group, carboxyl group, $C_1-C_6$ alkoxy group or halogen atom, and a salt thereof.

10. A method as defined in claim 9 wherein the compound is a compound of the formula (7) wherein [$R^8$, $R^9$ and $R^{10}$ are as defined in the formula (7) and] Aa is hydrogen, $C_1-C_6$ alkoxy, $C_1-C_6$ alkoxycarbonyl-$C_1-C_6$ alkyl, $C_1-C_6$ alkyl, halogen or $C_2-C_6$ alkenyl having $C_1-C_6$ alkoxycarbonyl group as the substituent.

* * * * *